(12) United States Patent
Veraitch et al.

(10) Patent No.: US 12,024,699 B2
(45) Date of Patent: Jul. 2, 2024

(54) SYSTEMS, DEVICES, AND METHODS FOR CELL PROCESSING

(71) Applicant: ORIBIOTECH LTD., London (GB)

(72) Inventors: Farlan Singh Veraitch, London (GB); Simon Collings, Berkshire (GB); Nicholas Brown, Berkshire (GB)

(73) Assignee: ORIBIOTECH LTD., London (GB)

( * ) Notice: Subject to any disclaimer, the term of this patent is extended or adjusted under 35 U.S.C. 154(b) by 96 days.

(21) Appl. No.: 16/735,626

(22) Filed: Jan. 6, 2020

(65) Prior Publication Data
US 2020/0255790 A1  Aug. 13, 2020

(30) Foreign Application Priority Data

Jan. 4, 2019 (GB) .................................... 1900107
Jan. 4, 2019 (GB) .................................... 1900108
(Continued)

(51) Int. Cl.
*C12M 1/42* (2006.01)
*C12M 1/00* (2006.01)
(Continued)

(52) U.S. Cl.
CPC ............ *C12M 35/04* (2013.01); *C12M 21/00* (2013.01); *C12M 29/00* (2013.01); *C12M 35/08* (2013.01); *C12M 37/04* (2013.01); *C12M 41/48* (2013.01)

(58) Field of Classification Search
CPC ...... C12M 35/04; C12M 21/00; C12M 29/00; C12M 35/08; C12M 37/04; C12M 41/48
See application file for complete search history.

(56) References Cited

U.S. PATENT DOCUMENTS 3,865,411 A   2/1975  Rowe et al.
4,253,500 A   3/1981  Williams
(Continued)

FOREIGN PATENT DOCUMENTS

CN   103255047 A   8/2013
CN   103937662 A   7/2014
(Continued)

OTHER PUBLICATIONS

International Search Report and Written Opinion issued for PCT/GB2020/050007, dated Apr. 3, 2020.
(Continued)

*Primary Examiner* — William H. Beisner
*Assistant Examiner* — Danielle B Henkel
(74) *Attorney, Agent, or Firm* — TraskBritt

(57) ABSTRACT

The disclosure relates to systems, devices and methods for at least one of cell and gene therapy manufacture. In some embodiments, a cell processing unit is provided and comprises a housing defining an enclosure into which a cell processing platform can be mounted, a platform mounting bracket within the housing and configured and arranged to receive and retain a cell processing platform, a drive apparatus configured and arranged to operatively engage and act upon a cell processing platform so as to move same with respect to the platform mounting bracket, and an actuator configured and arranged to exert a force on a container mounted into the cell processing platform so as to expel a contents from the container.

15 Claims, 19 Drawing Sheets

(30) Foreign Application Priority Data

| Jan. 4, 2019 | (GB) | ................................. | 1900109 |
| Jan. 4, 2019 | (GB) | ................................. | 1900111 |
| Jan. 3, 2020 | (WO) | ................ | PCT/GB2020/005009 |
| Jan. 3, 2020 | (WO) | ................ | PCT/GB2020/050007 |
| Jan. 3, 2020 | (WO) | ................ | PCT/GB2020/050008 |
| Jan. 3, 2020 | (WO) | ................ | PCT/GB2020/050010 |

(51) Int. Cl.
*C12M 1/12* (2006.01)
*C12M 1/36* (2006.01)

(56) References Cited

U.S. PATENT DOCUMENTS

| 4,867,172 | A | 9/1989 | Haber et al. |
| 6,655,655 | B1 | 12/2003 | Matkovich et al. |
| 6,679,529 | B2 | 1/2004 | Johnson et al. |
| 6,880,801 | B2 | 4/2005 | Matkovich et al. |
| 7,090,191 | B2 | 8/2006 | Matkovich et al. |
| 7,284,731 | B1 | 10/2007 | Johnson et al. |
| 8,133,165 | B2 | 3/2012 | Rosiello |
| 8,263,389 | B2 | 9/2012 | Poo et al. |
| 8,414,765 | B2 | 4/2013 | Uber et al. |
| 8,415,144 | B2 | 4/2013 | Wilson et al. |
| 9,005,181 | B2 | 4/2015 | Lynn et al. |
| 9,352,865 | B2* | 5/2016 | Kuehni ............. A61M 5/14216 |
| 2004/0149776 | A1 | 8/2004 | Feygin et al. |
| 2004/0173286 | A1* | 9/2004 | Azzolini .................. A61M 1/82 141/346 |
| 2005/0032205 | A1 | 2/2005 | Smith et al. |
| 2006/0154363 | A1 | 7/2006 | Horn |
| 2007/0224676 | A1 | 9/2007 | Haq |
| 2008/0118974 | A1* | 5/2008 | Martin .................... C12M 29/04 435/297.1 |
| 2011/0020856 | A1* | 1/2011 | Poo ......................... C12M 23/42 435/29 |
| 2011/0076756 | A1 | 3/2011 | Wright |
| 2014/0103077 | A1 | 4/2014 | Zumbrum |
| 2015/0028586 | A1 | 1/2015 | Gerst et al. |
| 2015/0252317 | A1* | 9/2015 | Lipkens ................. C12M 41/44 210/748.05 |
| 2015/0344161 | A1 | 12/2015 | Selker et al. |
| 2018/0142200 | A1* | 5/2018 | Mason .................. A61M 5/148 |
| 2018/0362910 | A1* | 12/2018 | Bores ..................... C12M 23/52 |
| 2020/0190457 | A1* | 6/2020 | Veraitch ................. C12M 41/12 |
| 2022/0064580 | A1* | 3/2022 | Veraitch ................. C12M 35/06 |
| 2022/0073854 | A1* | 3/2022 | Veraitch ................. C12M 23/14 |
| 2022/0098536 | A1* | 3/2022 | Veraitch ............... C12N 5/0636 |
| 2022/0106550 | A1* | 4/2022 | Veraitch ............... C12N 5/0636 |

FOREIGN PATENT DOCUMENTS

| EP | 0981389 | A1 | 3/2000 | |
| EP | 1297861 | A1 | 4/2003 | |
| EP | 2 489 435 | A2 | 8/2012 | |
| EP | 2 607 474 | A1 | 6/2013 | |
| GB | 2507944 | A | 5/2014 | |
| JP | 10-146824 | A | 6/1998 | |
| JP | 3499790 | B2 | 2/2004 | |
| WO | 87/06952 | A1 | 11/1987 | |
| WO | 98/50105 | A1 | 11/1998 | |
| WO | WO 98/52631 | A1 | 11/1998 | |
| WO | 03/46141 | | 6/2003 | |
| WO | WO 2005/123905 | A1 | 12/2005 | |
| WO | 2008/030597 | A2 | 3/2008 | |
| WO | 2008/089510 | A1 | 7/2008 | |
| WO | 2010/024906 | A1 | 3/2010 | |
| WO | WO 2011/103359 | A2 | 8/2011 | |
| WO | 2013/063550 | A1 | 5/2013 | |
| WO | 2013/147688 | A1 | 10/2013 | |
| WO | WO 2014/042827 | A2 | 3/2014 | |
| WO | WO 2015/138489 | A1 | 9/2015 | |
| WO | WO 2016/185221 | A1 | 11/2016 | |
| WO | WO-2016185221 | A1 * | 11/2016 | ............ A61M 5/148 |
| WO | WO 2017/216237 | A1 | 12/2017 | |
| WO | WO 2017/220948 | A1 | 12/2017 | |
| WO | WO 2018/087558 | A1 | 5/2018 | |
| WO | 2019/014306 | A2 | 1/2019 | |

OTHER PUBLICATIONS

International Search Report and Written Opinion issued for PCT/GB2020/050008, dated Mar. 27, 2020.
International Search Report and Written Opinion issued for PCT/GB2020/050009, dated Apr. 1, 2020.
International Search Report and Written Opinion issued for PCT/GB2020/050010, dated Mar. 27, 2020.
Great Britain Examination Report for Great Britain Application No. 1900107.2, dated Feb. 9, 2022, 4 pages.
Great Britain Examination Report for Great Britain Application No. 1900109.8, dated Feb. 28, 2022, 4 pages.
United Kingdom Patent Examination Report for United Kingdom Patent Application No. GB1900108.0, dated Jun. 14, 2023, 5 pages.

* cited by examiner

SYSTEMS, DEVICES, AND METHODS FOR CELL PROCESSING

RELATED APPLICATIONS

The present disclosure claims priority to and benefit of the following applications:
UK patent application no. GB1900107.2, filed Jan. 4, 2019;
UK patent application no. GB1900108.0, filed Jan. 4, 2019;
UK patent application no. GB1900109.8, filed Jan. 4, 2019;
UK patent application no. GB1900111.4, filed Jan. 4, 2019;
PCT application no. PCT/GB2020/050007, filed Jan. 3, 2020;
PCT application no. PCT/GB2020/050008, filed Jan. 3, 2020;
PCT application no. PCT/GB2020/050009, filed Jan. 3, 2020; and
PCT application no. PCT/GB2020/050010, filed Jan. 3, 2020.
Each of the above-identified applications, in its entirety, is herein incorporated by reference.

TECHNICAL FIELD

The present disclosure relates to cell processing, as well as to systems, devices, and methods for cell and gene therapy manufacture, including, for example, those directed to cell processing units, cell processing platforms, cell processing devices, tracking and sterile connections thereof.

BACKGROUND

Cell and gene therapy manufacturing processes are often complex and include manual or semi-automated steps across several devices. Equipment systems used in various steps (i.e., unit operations) of cell-based therapeutic products (CTP) manufacturing may include devices for cell collection, cell isolation/selection, cell expansion, cell washing and volume reduction, cell storage and transportation. The unit operations can vary immensely based on the manufacturing model (i.e., autologous versus allogenic), cell type, intended purpose, among other factors. In addition, cells are "living" entities sensitive to even the simplest manipulations (such as differences in a cell transferring procedure). The role of cell manufacturing equipment in ensuring scalability and reproducibility is an important factor for cell and gene therapy manufacturing.

In addition, cell-based therapeutic products (CTP) have gained significant momentum thus there is a need for improved cell manufacturing equipment for various cell manufacturing procedures, for example, but not limited to stem cell enrichment, generation of chimeric antigen receptor (CAR) T cells, and various cell manufacturing processes such as collection, purification, gene modification, incubation/recovery, washing, infusion into patient and/or freezing.

The culture or processing of cells typically requires the use of a device to hold the cells, for example, in an appropriate culture medium when culturing the cells. The known devices include shaker flasks, roller bottles, T-flasks and bags. Such bottles or flasks are widely used but suffer from several drawbacks. Chief among the problems are the requirement for transfer of cells without contamination when passaging or processing subsequently and the sterile addition of supplements and factors. The existing cell culture devices require re-supply of culture medium and oxygen for continued cell growth. Gas permeable cell culture devices are described in U.S. Pat. No. 8,415,144. However, such devices also require transfer of medium and/or cells in and out of the devices.

Collapsible cell processing devices for use in medicine are known; see, for example, U.S. Pat. No. 4,867,172 concerning a blood collector, or WO 2008/030597 concerning a canister liner for fluid collection. However, such devices are not fabricated or constructed for use in cell and/or gene therapy manufacturing unit operations (i.e., steps).

A key limiting factor in the production of cells or gene therapies for use in medicine is the absence of compact, automated closed systems for performing unit operations without contamination. For example, during cell culture, upstream or subsequent processing of cells, there is a risk of contamination when making additions to the culture vessel, or when removing cells or removing liquid samples. The operating systems are largely manual and hence expensive to operate. Multiple pieces of equipment are typically required to cover all of the non-cell culture steps, which involves many transfers, each of which is an opportunity for operator errors and contamination to occur. Furthermore with increasing manual operations comes increasing risk of manual errors and therefore the current labour-intensive processes lack the robustness required for the manufacture of clinical-grade therapeutics.

There is therefore a need for cell processing devices (e.g., multistep cell processors), which permit such processing, which avoids the requirement for constant movement of cells into fresh devices. For example, it would be advantageous if scale-up of cells in culture could be achieved without transfer of cells into a larger device as the cell population for any given culture increases.

Previous cell manufacturing devices use complex equipment, which is large and difficult to assemble. The devices use complex networks of tubing, valves and pumps to link elements of the equipment together.

The applicant now provides an improved cell and/or gene therapy processing equipment, which combines the advantages of the cell culture containers of the applicant's earlier applications (PCT/GB2016/051451 and PCT/GB2017/053389) (i.e., avoiding the need for pumps and the requirement for constant passaging of cells into fresh culture devices, holding vessels, tubes etc.) with the advantages conferred by having individually configurable cell and/or gene therapy processing devices. Together with an improved, closed cell processing unit, the improved device and container described herein permit a variety of unit processes to be performed within a single device or container having a smaller footprint and being less complex than existing equipment, as will be explained in more detail herein. Moreover, the cell processing containers described herein may maintain an aseptic connection without the prerequisite of a laminar flow cabinet, a glove box, or the like.

The applicant's earlier application (PCT/GB2016/051451) describes a cell culture container in which the wall element, being composed of a flexible material, is compressible with respect to its top and base sections. The cell culture container described therein is compatible with the cell processing unit and device described herein.

In a further earlier application (PCT/GB2017/053389) the applicant describes an improved version of a cell culture container, having at least one inlet and further comprising one or more auxiliary containers in fluid communication with the primary container. The cell culture container described therein is improved so as to be compatible with the cell processing unit and device described herein. Moreover, a connection between the cell culture container described therein and other components is improved, thereby maintaining an aseptic environment through the connection. In the earlier application (PCT/GB2017/053389), a laminar flow cabinet was required in order to ensure an aseptic environment during cell and/or gene therapy manufacture and/or processing. However, this can increase costs and result in a more labor-intensive process. Thus, the present application also aims to provide an aseptic connection between components, irrespective of the surrounding environment or atmosphere.

BRIEF SUMMARY

It is an object of certain aspects of the present disclosure to provide an improvement over the above-described techniques and known art; particularly to provide a cell processing unit, a cell processing platform, a cell processing device and a cell processing container and systems that facilitate flexible, compact, low cost, multistep cell processing while reducing the risk of contamination.

Some embodiments of the present disclosure are directed to each of (and combinations thereof):
- base units, sterile connectors, bellows, associated structure (e.g., locking plates), as well as cassette/cartridge/containers associated therewith;
- cell processing units for cell and/or gene therapy manufacture;
- cell processing systems and corresponding methods;
- cell processing platforms for use in one or more unit operations in cell and/or gene therapy manufacture;
- cell processing devices for use in one or more unit operations in cell and/or gene therapy manufacture; and
- cell processing containers for use one or more unit operations in cell and/or gene therapy manufacture, as well as cell processing systems comprising one or more of such cell processing containers and a multi-step method of performing one or more unit operations in cell and/or gene therapy manufacture.

In some embodiments, a cell processing unit for cell and gene therapy manufacture is provided and comprises a housing defining an enclosure into which a cell processing platform can be mounted, a platform mounting bracket within the housing and configured and arranged to receive and retain a cell processing platform, a drive apparatus configured and arranged to operatively engage and act upon a cell processing platform so as to move same with respect to the platform mounting bracket, and an actuator configured and arranged to exert a force on a container mounted into the cell processing platform so as to expel the contents from the container.

In such embodiments (as well as others), one and/or another (e.g., combinations of two or more) of the following additional features, functionality, steps, materials, structure and/or clarifications (together referred to as "features") is/are included, yielding yet further embodiments of the present disclosure:
- the platform mounting bracket comprises a mounting plate;
- the platform mounting bracket comprises a retaining flange spaced apart from the mounting plate (see above) in order that a cell processing platform is received and retained in position in the housing between the mounting plate and the retaining flange;
- the mounting plate is substantially C-shaped;
- the drive apparatus comprises a rotational drive apparatus configured and arranged to operatively engage and act upon a cell processing platform so as to rotate same with respect to the platform mounting bracket, where:
  - the rotational drive apparatus comprises a drive wheel, which is mounted on the platform mounting bracket and is configured to engage a surface of a cell processing platform and to impart rotational movement on it;
  - the rotational drive apparatus comprises a sprung wheel biased toward the drive wheel and spaced apart from it and mounted on the platform mounting bracket; and/or
  - the rotational drive apparatus comprises a hinged wheel biased toward the drive wheel and spaced apart from it and mounted on the platform mounting bracket, where the hinged wheel, in some embodiments, is moveable into an open position in which a cell processing platform is inserted into and engaged with the cell processing platform mounting bracket and a closed position in which the hinged wheel is engaged with a surface of the cell processing platform in order to retain same in the cell processing platform mounting bracket;
- the actuator is a linear actuator comprises a plunger operatively coupled to a drive motor, where the plunger, in some embodiments, is configured to engage a container in the cell processing platform and to exert a compression force on the container;
- a primary actuator configured and arranged to exert a force on a primary container mounted to the cell processing platform so as to expel a fluid from the container, where the primary actuator comprises a linear actuator, and/or comprises a plunger operatively coupled to a drive motor, where the plunger is, in some embodiments, configured to engage a primary container mounted to the cell processing platform and to exert a compression force on the primary container;
- a valve actuator operable to act upon a pinch valve in the cell processing platform so as to open and close same as force is applied to the container, where the valve actuator, in some embodiments, is a linear actuator, and/or a solenoid valve;
- a location detecting sensor operable to detect the position of the cell processing platform relative to the platform mounting bracket, where the location detecting sensor is operable to detect the rotational position of the cell processing platform relative to the platform mounting bracket, and comprises a Hall Effect sensor (for example);
- a home location detecting sensor operable to detect a home position of the cell processing platform relative to the platform mounting bracket, where the home location detecting sensor is operable to detect a single rotational position of the cell processing platform relative to the platform mounting bracket, and comprises a Hall Effect Sensor, such that, voltage detected by the Hall Effect sensor is greater at the home position of the cell processing platform relative to the platform mounting bracket than at any other position during the rotation of the cell processing platform relative to the platform mounting bracket;
- the container is compressible;

the container comprises a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material;

the primary container is compressible, and may comprise a cell processing container;

the primary container comprises a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material;

the container(s) is one of: a reagent container, a bioreactor, a cell culture container, a waste container, a filter, an electroporator, a purifier, holding container, apheresis/leukopheresis, differentiation chamber, chromatography column, settling chamber, sieve, shaking/mixer, a centrifuge and a magnetic bead separator or the like; and control of the device is automated.

In some embodiments, a cell processing container for use in one or more unit operations in cell and/or gene therapy manufacture is provided, where the container has a base section, a top section arranged substantially in parallel with the base section and a wall element arranged between the top section and the base section and defining an internal lumen of the container, in which the wall element of the cell processing container preferably is compressible with respect to the top and base section and the wall element of the cell processing container is composed of a flexible material, wherein the cell processing container comprises at least one sterile connector end configured to operatively couple with a further sterile connector end so as to form a sterile connector between the cell processing container and a further component to which the cell processing container is to be fluidly connected.

In such embodiments (as well as others), one and/or another (e.g., combinations of two or more) of the following additional features, functionality, steps, materials, structure and/or clarifications (together referred to as "features") is/are included, yielding yet further embodiments of the present disclosure:

the at least one sterile connector end is a genderless sterile connector end configured to operatively couple with a further genderless sterile connector end;

the at least one sterile connector end is a male sterile connector end configured to operatively couple with a female sterile connector end;

the at least one sterile connector end is a female sterile connector end configured to operatively couple with a male sterile connector end;

a plurality of sterile connector ends each configured to operatively couple with a separate further sterile connector end to form a plurality of sterile connectors between the cell processing container and at least one further component to which the cell processing container is to be fluidly connected;

the sterile connector ends are embedded in the cell processing container;

the sterile connector end is operatively coupled to a pinch valve embedded in the cell processing container;

the cell processing container has a circular, square, rectangular, elliptical, or triangular cross section;

the cell processing container has a circular shape, the sterile connector end(s) is/are connected to the top and/or base section of the cell processing container in an essentially circular pattern;

and one or more auxiliary containers detachably connected to the cell processing container, where the one or more of the auxiliary containers comprise the further sterile connector end and is connected to the cell processing container via the further sterile connector end;

the one or more of the auxiliary containers is/are located on the top section of the cell processing container;

the one or more of the auxiliary containers is/are located at or near the base section of the cell processing container; and/or the one or more auxiliary containers have a base section, a top section arranged substantially in parallel with the base section and a wall element arranged between the top section and the base section and defining an internal lumen of the container, in which the wall element of the auxiliary container preferably is compressible with respect to the top and base section and the wall element of the auxiliary container is composed of a flexible material.

In some embodiments, a multi-step method of performing one or more unit operations in cell and/or gene therapy manufacture using a cell processing system according to any of the embodiments disclosed herein. In some such embodiments, the method includes (in some embodiments) introducing a cell population of interest into the cell processing container and sequentially adding one or more reagents from one or more auxiliary containers into the cell processing container in order to effect the desired one or more unit operations in cell and/or gene therapy manufacture.

In some embodiments, a cell processing device for use in performing one or more unit processes in cell and/or gene therapy manufacturing, comprising a cell processing platform fluidly coupled to at least one auxiliary container and to at least one primary container, the cell processing platform comprising a body portion comprising at least one fluid inlet fluidly connected to a fluid outlet, and an auxiliary container port fluidly coupled to the at least one fluid inlet of the body portion, wherein the at least one auxiliary container is received in sealing engagement with the auxiliary container port such that the auxiliary container lumen is fluidly connected with the at least one fluid inlet of the body portion, and a primary container is received in sealingly engagement with the primary container port such that the primary container lumen is fluidly connected with the fluid outlet of the body portion.

In such embodiments (as well as others), one and/or another (e.g., combinations of two or more) of the following additional features, functionality, steps, materials, structure and/or clarifications (together referred to as "features") is/are included, yielding yet further embodiments of the present disclosure:

the auxiliary container port comprises a container receiving sleeve connected to the body portion and being configured to surround at least a portion of the auxiliary container, which portion comprises the fluid outlet of the container;

the cell processing platform comprises a plurality of auxiliary container ports and each one of a plurality of auxiliary containers are received in sealing engagement with one of the plurality of auxiliary container ports such that the lumen of each auxiliary container is fluidly coupled with a fluid inlet of the body portion;

each auxiliary container port is coupled to a separate fluid inlet of the body portion, each separate fluid inlet of the body portion is (in some embodiments) fluidly connected to a fluid outlet of the body portion, and the at least one fluid inlet and the fluid outlet of the body portion is fluidly coupled to one another by a fluid conduit;

the fluid conduit comprises a valve operable to open and close the fluid conduit, and the valve is one of: a pinch valve, a pressure-sensitive valve, a clamp valve, a membrane valve, a rupture disc, a venous valve and an aperture valve;

each auxiliary container port comprises a container filling port, where the container filling port, in some embodiments, is fluidly connected to a fluid inlet of the auxiliary container port, and each container filling port (in some embodiments) comprises a valve operatively coupled to the fluid inlet and a fluid outlet of the auxiliary container port and operable to control fluid flow direction through the auxiliary container port;

the container filling port comprises a valve operable, in an open position, to allow fluid to flow to the fluid inlet of the auxiliary container port and not to the fluid outlet of the auxiliary container port and, in a closed position, to close the container filling port and to allow fluid to flow from the fluid inlet of the auxiliary container port to the fluid outlet of the auxiliary container port;

the at least one auxiliary container comprises a mating element configured to fluidly connect to a corresponding mating element on the auxiliary container port, where the mating element is at least one of: a sterile connector end or a LuerLok™;

the primary container port comprises a mating element configured to fluidly connect to a corresponding mating element on the primary container, where the mating element comprises at least one of: a sterile connector end or a LuerLok™;

the auxiliary container port comprises a sterile connector end at the fluid inlet and/or the fluid outlet of the auxiliary container port, where each sterile connector end, in some embodiments, is configured to engage with a further sterile connector end on a container and/or on the body portion respectively;

the fluid outlet of the body portion comprises a sterile connector end, which may be configured to engage with a further sterile connector end on the primary container attachable to the body portion;

at least one positional tracking device (and in some embodiments, a plurality) configured to be operable to indicate a set location on the platform, where the positional tracking device can be one or more of: a magnet, an RFID sensor, a light sensor or a cog operable to engage a further cog;

the at least one positional tracking device is located relative to the auxiliary container port such that the location of the positional tracking device is related to the position of the auxiliary container port;

the at least one positional tracking device is located on the body portion relative to the auxiliary container port;

a sampling port located in the body portion;

a gas transfer port located in the body portion;

the auxiliary container port configured, for example, to receive an auxiliary container having a base section, a top section arranged substantially in parallel with the base section and a wall element arranged between the top section and the base section and defining an internal lumen of the container, and the wall element of the container can be (and in some embodiments, preferably) compressible with respect to the top and base section and the wall element of the container can be composed of a flexible material;

the primary container port is configured to receive a primary container having, for example, a base section, a top section arranged substantially in parallel with the base section and a wall element arranged between the top section and the base section and defining an internal lumen of the container, and the wall element of the container can be (and in some embodiments, preferably) compressible with respect to the top and base section and the wall element of the container can be composed of a flexible material;

the primary container includes an attachment flange that is mounted to the top section of the primary container and is configured to sealingly engage and mount to the primary container port;

the at least one auxiliary container is compressible;

the at least one auxiliary container is any of: a syringe or any shaped container with a moving seal allowing variable volume operations;

the at least one auxiliary container is a bag, which can be retained in a frame and can be moveable with respect to the frame;

one or more auxiliary containers detachably connected to an auxiliary container port of the cell processing platform, where one or more of the auxiliary containers, in some embodiments, is/are connected to a respective auxiliary container port with a sterile connector;

the at least one auxiliary container is located on the top of the cell processing platform;

the primary container is located on the bottom of the cell processing platform;

the auxiliary container is one of: a reagent container, a cell culture container, a waste container, a filter, an electroporator, a purifier, a waste container, a filter, an electroporator, a purifier, holding container, apheresis/leukopheresis, differentiation chamber, chromatography column, settling chamber, sieve, shaking/mixer, a centrifuge and a magnetic bead separator or a bioreactor;

and the primary container is a reagent container, a bioreactor, a cell culture container, a waste container, a filter, an electroporator, a purifier, a waste container, a filter, an electroporator, a purifier, holding container, apheresis/leukopheresis, differentiation chamber, chromatography column, settling chamber, sieve, shaking/mixer, a centrifuge and a magnetic bead separator or the like, a centrifuge and a magnetic bead separator or the like.

In some embodiments, a cell processing platform for use in one or more unit operations in cell and/or gene therapy manufacture is provided, where the platform includes a body portion comprising at least one fluid inlet fluidly connected to a fluid outlet, and an auxiliary container port fluidly coupled to the at least one fluid inlet of the body portion, where the auxiliary container port is configured and arranged to receive and sealingly engage with an auxiliary container and to fluidly connect the auxiliary container lumen with the at least one fluid inlet of the body portion, and a primary container port configured and arranged to sealingly engage with a primary container and to fluidly connect the primary container lumen with the fluid outlet of the body portion.

In such embodiments (as well as others), one and/or another (e.g., combinations of two or more) of the following additional features, functionality, steps, materials, structure and/or clarifications (together referred to as "features") is/are included, yielding yet further embodiments of the present disclosure:

- the auxiliary container port comprises a container receiving sleeve connected to the body portion and, in some embodiments, is configured to surround at least a portion of the auxiliary container, which portion comprises the fluid outlet of the container;
- the auxiliary container port comprises a mating element configured to fluidly connect to a corresponding mating element on an auxiliary container, where the mating element is at least one of: a sterile connector end or a Luer Lok™ (for example);
- the primary container port comprises a mating element configured to fluidly connect to a corresponding mating element on a primary container;
- the mating element comprises at least one of: a sterile connector end or a LuerLok™ (for example);
- the auxiliary container port comprises a sterile connector end at the fluid inlet and/or the fluid outlet of the auxiliary container port, each sterile connector end, in some embodiments, is configured to engage with a further sterile connector end on a container and/or on the body portion respectively;
- the fluid outlet of the body portion comprises a sterile connector end configured to engage with a further sterile connector end on a primary container attachable to the body portion;
- the body portion is substantially hollow;
- the at least one fluid inlet and the fluid outlet of the body portion are fluidly coupled to one another by a fluid conduit;
- the fluid conduit comprises a valve operable to open and close the fluid conduit, where the valve is any of: a pinch valve, a pressure-sensitive valve, a clamp valve, a membrane valve, a rupture disc, a venous valve and an aperture valve;
- the auxiliary container port comprises a container filling port, and the container filling port, in some embodiments, is fluidly connected to a fluid inlet of the auxiliary container port;
- the container filling port comprises:
  - a valve operatively coupled to the fluid inlet and a fluid outlet of the auxiliary container port and operable to control fluid flow direction through the auxiliary container port;
  - a valve operable, in an open position, to allow fluid to flow to the fluid inlet of the auxiliary container port and not to the fluid outlet of the auxiliary container port and, in a closed position, to close the container filling port and to allow fluid to flow from the fluid inlet of the auxiliary container port to the fluid outlet of the auxiliary container port;
- a plurality of auxiliary container ports each configured and arranged to receive and sealingly engage with an auxiliary container and to fluidly connect the container lumen with a fluid inlet of the body portion;
- each auxiliary container port is coupled to a separate fluid inlet of the body portion;
- each separate fluid inlet of the body portion is fluidly connected to a fluid outlet of the body portion;
- at least one positional tracking device (and in some embodiments, a plurality) operable to indicate a set location on the platform, where, in some embodiments, the positional tracking device is at least one of: a magnet, an RFID sensor, a light sensor or a cog operable to engage a further cog;
- the at least one positional tracking device is located relative to the auxiliary container port such that the location of the positional tracking device is related to the position of the auxiliary container port;
- the at least one positional tracking device is located on the body portion relative to the auxiliary container port;
- a sampling port in the body portion;
- a gas transfer port in the body portion;
- the auxiliary container port is configured to receive a container having a base section, a top section arranged substantially in parallel with the base section and a wall element arranged between the top section and the base section and defining an internal lumen of the container, in which (in some embodiments) the wall element of the container preferably is compressible with respect to the top and base section and the wall element of the container is composed of a flexible material;
- the primary container port is configured to receive a primary container having a base section, a top section arranged substantially in parallel with the base section and a wall element arranged between the top section and the base section and defining an internal lumen of the container, in which (in some embodiments) the wall element of the container preferably is compressible with respect to the top and base section and the wall element of the container is composed of a flexible material;
- the primary container further comprises an attachment flange mounted to the top section of the primary container and being configured to sealingly engage and detachably mount to the primary container port.

In some embodiments, the container is a container described in the applicant's earlier patent application PCT/GB2016/051451.

In some embodiments, the container is a container described in the applicant's earlier patent application PCT/GB2017/053389.

In some embodiments, a cell processing method is provided, configured for at least one of cell and gene therapy manufacture. The method includes introducing a cell population of interest into a primary container of a cell processing platform, sequentially adding one or more reagents from one or more auxiliary containers to the primary container in order to effect at least one of a desired growth, culturing and modification of the cell population, culturing the cell population of interest in the primary container, and exerting a force on the container so as to expel contents from the container.

In such embodiments (as well as others), one and/or another (e.g., combinations of two or more) of the following additional features, functionality, steps, materials, structure and/or clarifications (together referred to as "features") is/are included, yielding yet further embodiments of the present disclosure:

- the force is applied via an actuator comprising a bellows or a plunger,
- the cell processing platform is mounted within a housing of a cell processing unit,
- tracking and/or detecting at least one of a position and location of the cell processing platform;

driving the cell processing platform, where driving, in some embodiments, comprises rotating the cell processing platform, and, in some embodiments, rotation is imparted on a surface of the cell processing platform via a drive-wheel;

force comprises compression;

connecting the cell processing platform with at least one other additional cell processing platform, or an additional component via a sterile connector, and the connector, in some embodiments, fluidly connects the cell processing platform with the at least one other additional cell processing platform or an additional component;

a genderless sterile connector configured to connect to a further sterile connector end;

a/the connector is configured to connect to the container of the cell processing platform, where the sterile connector, in some embodiments, is a genderless sterile connector;

tracking comprises tracking a plurality of cell processing platforms;

sampling the contents of the container;

transferring at least one gas into or out of the container; and sealingly engaging the container with a second container.

As will be clear to the person skilled in the art, elements, components, features and advantages of disclosed cell processing units, cell processing platforms, cell processing devices, cell processing containers, sterile connector/s/ends, and associated methods of manufacture, usage, and components thereof may be applied equally to various embodiments described herein. That is, where a feature is described in relation to one embodiment, aspect or example, this is not intended to preclude the inclusion of such a feature in relation to another embodiment, aspect or example, as will be recognized by those skilled in the art.

BRIEF DESCRIPTION OF THE DRAWINGS

These and other aspects, features and advantages of which embodiments of the disclosure are capable of, will be apparent and elucidated from the following description of embodiments and aspects of the present disclosure, reference being made to the accompanying drawings, in which.

In the drawings, like reference numerals refer to like parts.

DETAILED DESCRIPTION

Cell Processing Unit

Figure 1:
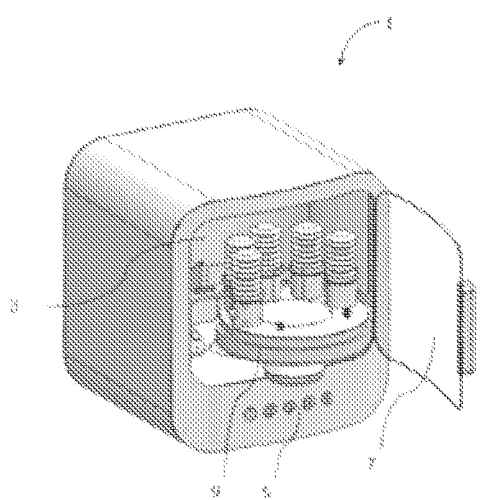
FIG. 1 illustrates a perspective view of a cell processing unit according to an embodiment of the disclosure with a cell processing device partially loaded into the device.

FIG. 1 illustrates a cell processing unit 1 according to the present disclosure. The cell processing unit comprises a housing 2 formed of four walls upstanding from a base wall and a top wall parallel to the base wall and spaced apart from it by the length of the walls. The housing 2 forming a chamber 3 with a hinged door 7 in one wall for receiving a cell processing device 901 comprising cell processing platform (CPP) 9. On the front panel of the cell processing unit 1 is a control panel 5 to enable the user to program and control various features positioned within the chamber 3, as well as their interactions with the cell processing device 901. Details of these features and the cell processing device 901 are set out in more detail below.

The cell processing unit 1 has a housing 2 that defines an enclosed space, being chamber 3 in which one or more unit operations (i.e., steps) of cell and/or gene therapy manufacturing process can occur.

Figure 2:
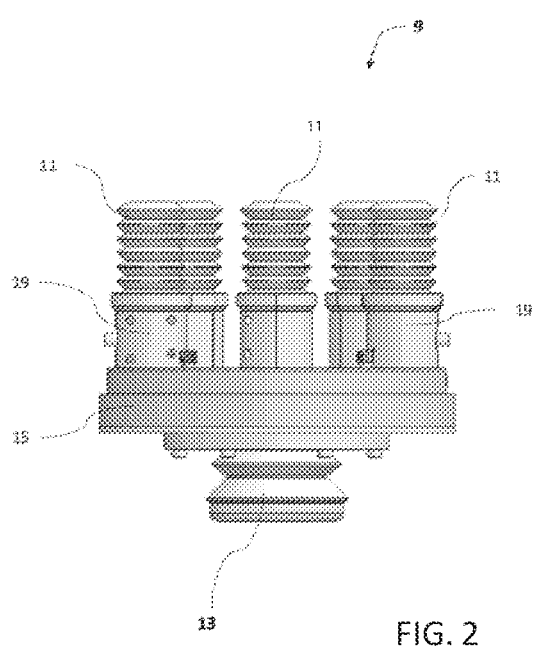
FIG. 2 illustrates a side view of a cell processing device according to an embodiment of the disclosure.

An automated cell processing system according to an embodiment of the disclosure comprises cell processing unit 1 and a cell processing device 901 as shown in FIG. 2. The cell processing device 901 comprises a cell processing platform 9 and one or more auxiliary containers 11 coupled to the cell processing platform 9. The cell processing platform 9 can be manipulated by the cell processing unit 1 to transfer liquids between the auxiliary container 11 (e.g., feed bellows) located on the top of the cell processing platform 9 and the primary or cell processing container 13 (e.g., reactor bellows) located on the bottom of the cell processing platform 9. FIG. 1 shows an embodiment in which the cell processing system has cell processing unit 1 and a cell processing device 901 with five auxiliary containers 11 fluidly connected to the cell processing platform 9. The cell processing unit 1 rotates the cell processing platform 9 using a friction drive system. The cell processing unit 1 comprises a valve solenoid micro-linear actuator (38, FIG. 6), which, when activated, opens pinch valves 27 in the cell processing platform 9 and presses the auxiliary container 11 using a linear actuator (106, FIG. 6). The cell processing platform 9 comprises a body portion comprising base plate or body portion 15 onto which the primary container 13 (e.g., reactor bellows) is fitted on the underneath into a primary container port (FIG. 2, reference numeral 14) and the five auxiliary containers 11 (e.g., feed bellows) are fitted on top of the base plate 15 in auxiliary container ports 19. The auxiliary containers 11 (e.g., feed bellows) are mounted on top of the sleeves forming the auxiliary container ports 19 that contain Luer Lok™ fittings to connect the auxiliary containers 11 to the tubing in the auxiliary container ports 19. The tubing being fluidly connected to the tubing in the base plate 15, through the base plate 15 and onto the fluid outlet at the primary container port 14. Each auxiliary container port 19 comprises a filling valve 31, which allows for filling of the auxiliary container 11 fluidly coupled to the auxiliary container port 19. The base plate 15 of the cell processing platform 9 contains normally closed pinch valves 27 acting on the flexible tubing 29 between the auxiliary containers 11 and the primary container 13. In this embodiment, the cell processing system comprises a cell processing device with five auxiliary containers. However, it should be appreciated that in cell processing device may have a different number of auxiliary containers according to the present disclosure. It is further envisaged that the containers may have different volumes according to the present disclosure.

The chamber 3 is not sterile, however the containers are completely closed when loaded into the cell processing platform. The containers in parallel and/or series in the cell processing platform provide a single closed consumable unit (cell processing device) for the entire manufacturing process. Filling the containers occurs either aseptically (e.g., in a laminar flow hood) or using sterile connections (e.g., tube welding or sterile connections).

The housing 2 of the cell processing unit 1 allows for easy insertion and removal of the cell processing device 901 through a front opening door 7. With the door 7 open, the cell processing device 901 comprising the cell processing platform 9 and attached auxiliary containers 11 each comprising various cell processing reagents can be placed down and slid into its final position. The control panel 5 is located on the front of the housing 2, meaning that all interactions with the cell processing unit 1 happen from the front. In this way, multiple cell processing units 1 can be placed close together, side by side or on top of each other. Having rows of units or stacks of units, respectively, facilitates the capacity for advanced manufacturing and processing. The depicted embodiment is shown with five buttons, one for each feed actuation in a test protocol for the system. The door 7 is transparent so that the operations can be visible when demonstrating the function of the apparatus. In alternative embodiments an opaque door could be provided. In this way, the cells can be shielded from UV light during processing.

Figure 6:
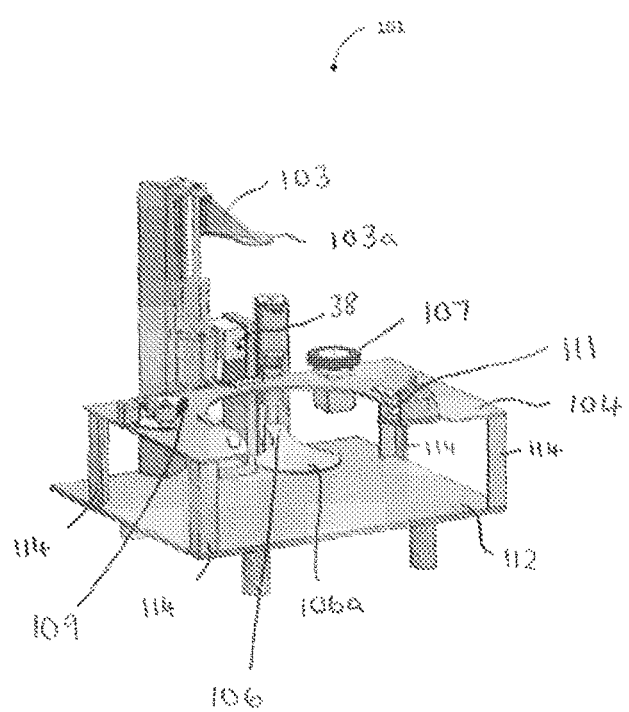
FIG. 6 illustrates a perspective view of the mounting bracket, actuators and frictional drive mechanism of the cell processing unit of FIG. 1.

FIG. 6 shows a portion 101 of cell processing unit 1 with the housing 2 removed for ease of depiction. Inside the housing the portion of the cell processing unit 101 comprises a linear actuator 103 for compression of the auxiliary container 11 feed bellows, a linear actuator 106 for compression of the primary container 13 reactor bellows, a frictional drive mechanism (107, 109, 111) mounted on mounting plate 104 and operable to rotate the cell processing platform 9 and a micro linear actuator 38 for opening the pinch valves, which are operable to open and close the tubing in the platform. The internal structure of the apparatus is machined from aluminum; the linear actuators 106, 103 are aluminum and steel constructions with the lead screws hard coated in TFE dry lubricant.

In addition to the mounting plate 104, the mounting bracket comprises a mounting flange (not shown), located above the mounting plate in such a way as to retain the cell processing platform by frictional fit between the mounting plate 104 and the mounting flange.

The layout of the actuators 38, 103, 106 allows them to be hidden in the rear of the apparatus by a cover (not shown) through which only the plungers 103a, 106a protrude to compress the bellows of the auxiliary and primary containers respectively, helping to give a clean and uncomplicated appearance, and provides an apparatus that is simpler to clean and wipe down. A power supply and the electronics for the actuators and the frictional drive mechanism are mounted on the plate 112 below the mounting plate 104. The four risers 114 are adjustable in height and operable to change the distance between the mounting plate 104 and the riser 114 housing the power supply and the electronics. In this way, the apparatus can accommodate different sizes of primary containers.

The housing 2 contains all of the actuators and electronics necessary to manipulate the cell processing device. The feed bellows plunger 103a and reactor plunger 106a operable to exert a compression force on the auxiliary container and the primary container respectively, attach to linear rails, each with a maximum force of 100N. The motors driving the linear rails are bipolar stepper motors. The valve actuator 38 is a linear actuator with a maximum force of 45N.

The frictional drive mechanism (107, 109, 111) comprises a drive wheel 107 located on mounting plate 104 and operable to impart rotation on the cell processing device. The drive wheel 107 is a bipolar stepper motor. The actuator stepper motors on the linear rails and the stepper motor in the frictional drive mechanism are driven by a control system and associated power supply (not shown).

Figure 7:
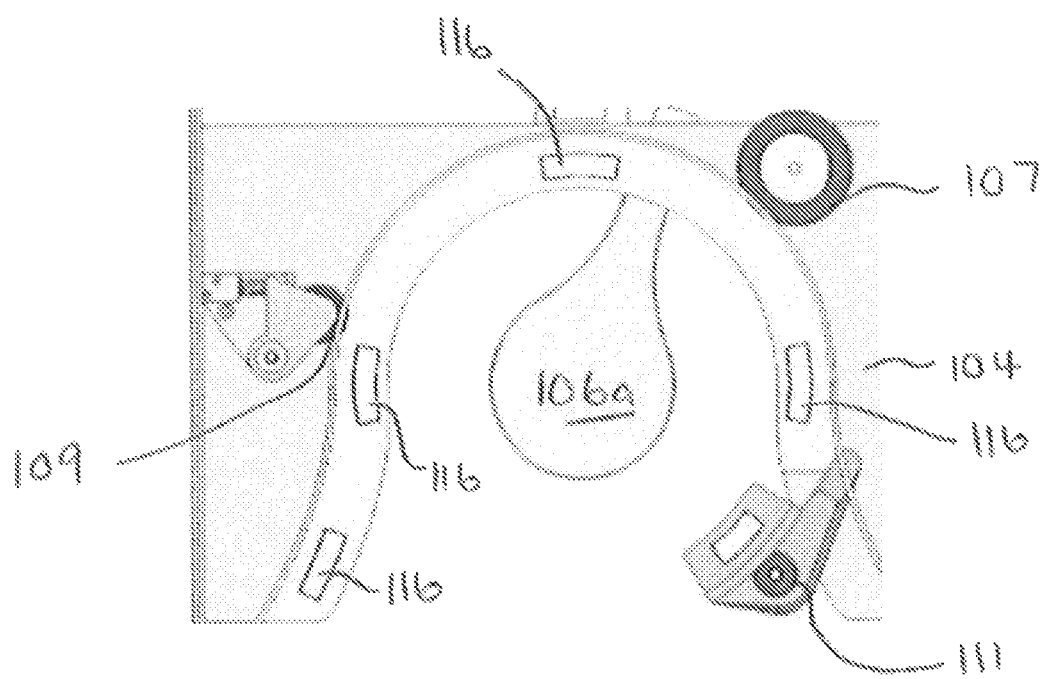
FIG. 7 illustrates a top view of the mounting plate and the frictional drive mechanism of the partial cell processing unit of FIG. 6.

FIG. 7 shows the elements of the frictional drive mechanism (107, 109, 111) mounted to the mounting plate 104 of the mounting bracket. To allow the cell processing device 901 comprising the cell processing platform 9 and the auxiliary containers to be inserted from front only, a drive method has been developed where the cell processing platform 9 is held between three friction wheels, one of which being driven 107, the other spring loaded and the third being a hinge wheel 111 within the door, which opens to allow insertion of the cell processing platform 9 and closes to lock it in place. The cell processing device 901 rotates on low friction PTFE pads 116 on the mounting plate 104. The spring force of the sprung frictional wheel 109 will be such that there is no slip between the drive wheel 107 and the outer face of the base plate 15 of the cell processing platform 9. The driven wheel 107 is directly connected to a stepper motor. The base plate 15 of the cell processing platform 9 is fitted with a series of magnets 118 around its circumference so that its position can be read by a Hall Effect sensor 120 mounted on the mounting plate 104. The cell processing platform 9 therefore acts like an encoder and gives closed loop position feedback independent of any motor slip.

Figure 8:
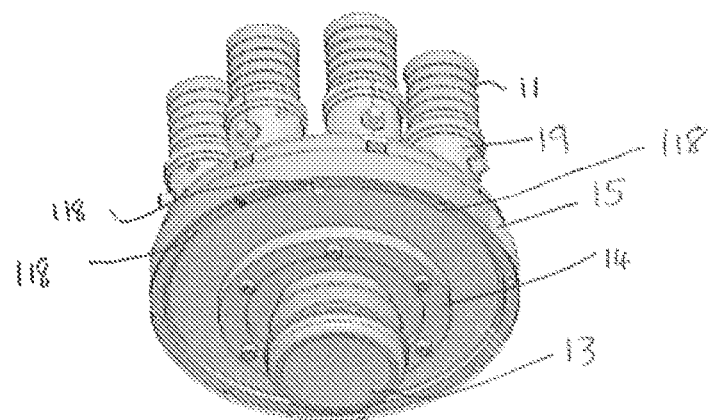
FIG. 8 illustrates a perspective view of the underside of the cell processing device of FIG. 2.
Figures 9, 10:
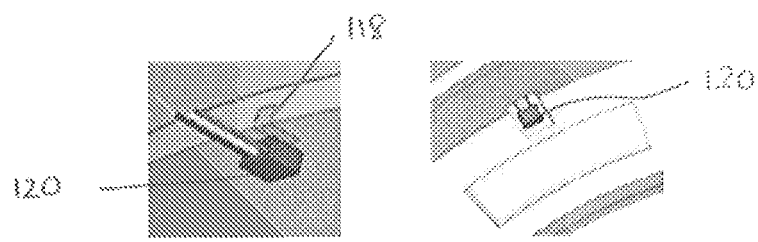
FIG. 9 illustrates a close-up view of the cell processing device and sensor arrangement of FIG. 8.
FIG. 10 illustrates a top view of the cell processing device and sensor arrangement of FIG. 8.
Figure 11:
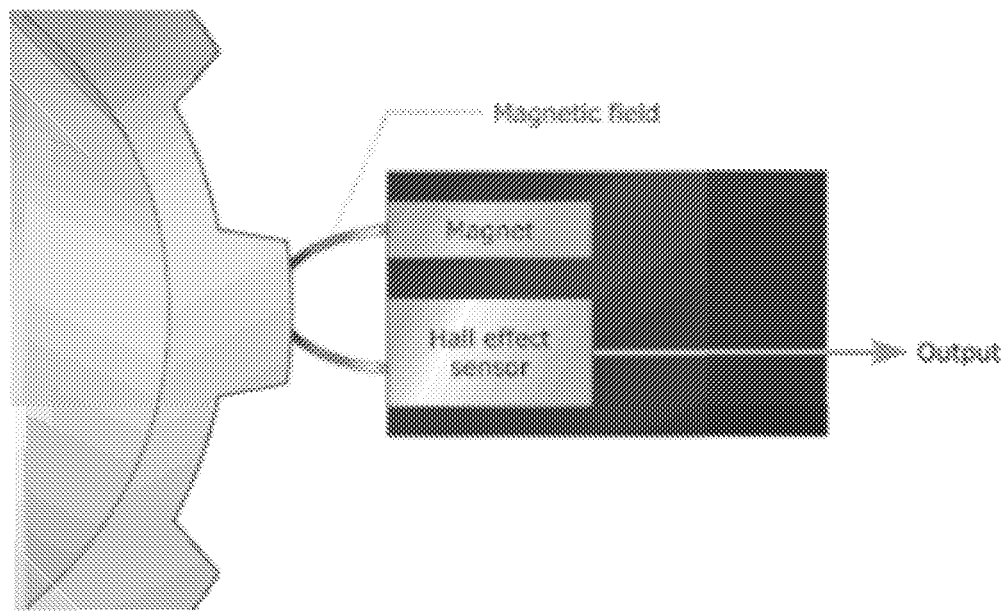
FIG. 11 illustrates a Hall Effect Sensor of the cell processing unit and a cell processing platform comprising at least one magnet.

The Hall Effect sensor 120 mounted to the mounting plate 104 attached to the housing 2 is operable to detect the magnetic field from the magnets 118 on a cell processing platform 9 mounted in the housing 2. The Hall Effect sensor 120 is operable to detect the position of the cell processing platform 9 relative to the mounting plate 104. As best seen in FIG. 8, each auxiliary container port 19 attached to the base plate 15 of the cell processing platform 9 has a magnet 118 positioned in the base plate 15 adjacent the auxiliary container port 19. In this way, the Hall Effect sensor 120 will detect a magnet 118 when an auxiliary container port 19 and its associated magnet 118 is in line with the sensor. Therefore, the respective auxiliary container port 19 is in a known position in the housing relative to the mounting plate 104.

FIGS. 8, 9, 10 and 11 show the positional sensor array operable to detect the position of the cell processing platform 9 of the cell processing device within the cell processing unit 1.

The sensor array comprises Hall Effect sensors 120 and a series of magnets 118 on the base plate 15. The sensor array tracks the position of the cell processing platform 9 using the Hall Effect sensors 120. The Hall Effect sensors 120 produces a voltage in response to magnetic fields produced by magnets 118. There are two Hall Effect sensors 120 mounted to the mounting plate 104 in the housing 2 and a series of magnets 118 embedded in the cell processing platform 9. One of the Hall Effect sensors 120 is for tracking rotation of the cell processing platform 9 relative to the mounting plate 104 and the other Hall Effect sensor 120 is dedicated to tracking a so-called home position of the cell processing platform 9 relative to the mounting plate 104. The home position is determined by having one magnet 118 on a different pitch circle diameter to the other magnets 118 on the cell processing platform 9, serving as an index or marker to count full revolutions of the cell processing platform 9 in the housing 2. Using the cell processing device as an encoder, rather than having an encoder on the motor, means that there is a closed loop position feedback on the cell processing device itself.

To ensure there will be no slip between the drive mechanism and the cell processing platform 9, the friction between the elastomeric driving (friction) wheel 107 and the base plate 15 needs to be greater than the friction between the PTFE pads 116 and the base plate 15. Using the maximum force that will be transmitted between the drive wheel 107 and the base plate 15 of the cell processing platform 9, the normal force required to ensure consistent drive can be calculated.

Cell Processing Device

The cell processing platform 9, as shown in FIGS. 2-5, comprises a cell processing platform having an annular base plate 15 with a number of auxiliary container ports 19, in this case five, arranged on the upper surface, and a single primary or reaction container 13 mounted on its underside at a primary container port 14. Each auxiliary container port 19 is adapted to receive an auxiliary container 11, such as the types described herein, or in the applicants' earlier publication WO2018087558. Each of the auxiliary containers 11 in the example has a 45 ml maximum capacity such that the total feed capacity of the five auxiliary containers 11 is 225 ml. The primary container 13 has a maximum capacity of 150 ml.

Figure 3:
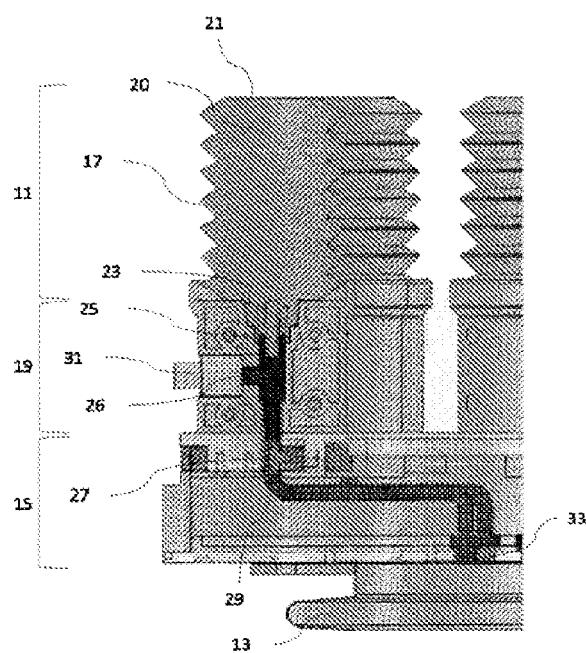
FIG. 3 illustrates a cross-sectional view of a part of the cell processing device of FIG. 2.

As shown in the cross-section of FIG. 3, the auxiliary container 11 comprises a top section 21 and a base section 23 with a collapsible bellows portion 17 located between them to define a storage volume 20. The base section 23 includes fluid outlet 25 through which the contents of the storage volume 20 can be transferred. With the auxiliary container 11 located into auxiliary container port 19, the fluid outlet 25 is in fluid communication with a connector 26 located therein. In the example shown, the connector 26 comprises a 4-way stopcock described in more detail below.

The auxiliary containers 11 are formed of blow molded LDPE while the auxiliary container ports 19 are formed of Nylon. The base plate 15 is formed of machined HDPE and the primary container 13 is formed of blow molded HDPE bonded to a machined HDPE flange being the primary container port 14. The base plate 15 is made up of three pieces that are screwed together. The primary container 13 is mounted to the base plate 15 by screws.

A flexible tubing 29 comprises a first end fitted to connector 26, and a second end fitted to base plate outlet 33, thereby forming a fluid communication conduit between the auxiliary container 11 and the primary container 13. The flexible tubing 29 may comprise any appropriate length and cross section. In the example show, the flexible tubing 29 is COLE-PARMER® Platinum Cured Silicone Tubing with inner diameter (ID) ⅛" and outer diameter (OD) 3/16". Aptly, the flexible tubing will be made from a suitably non-leachable, resilient and biologically inert material, in this case silicone, although other resilient materials may be used.

Fluid flow through the fluid communication conduit, and hence between an auxiliary container 11 and the primary container 13 is controlled by valve means 27, located within the base plate 15. In the example shown, the auxiliary container 11 is one of several, each located in a corresponding auxiliary container port 19 on the base plate 15. Accordingly, each auxiliary container 11 is provided with a unique flexible tubing 29 to the primary container 13, controlled by a separate valve means 27. In this way, the transfer of the contents of each storage volume 20 may be precisely and independently controlled.

Figure 4A:
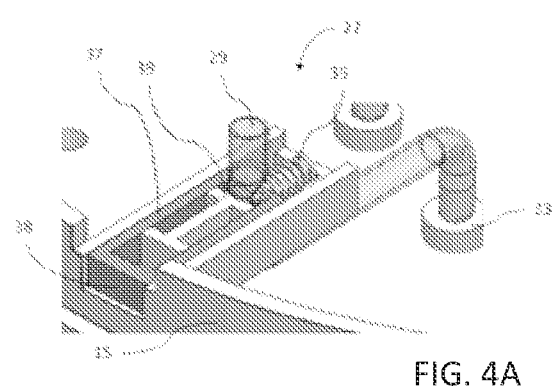
FIGS. 4A and 4B illustrate a perspective view of the valve means of the cell processing platform of the cell processing device of FIG. 2.
Figure 4B:
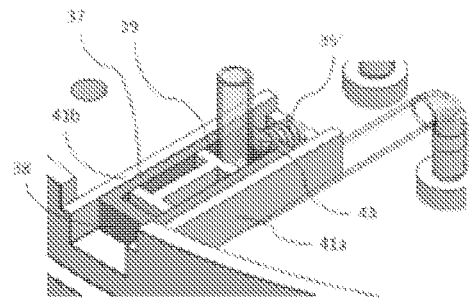

One of the valve means 27 is shown in more detail in FIGS. 4A and 4B. The valve means 27 comprises a closure portion of sterile connector end 37 slidably engaged within a radial channel located in the base plate 15 and defined between channel walls 41*a* and 41*b*. The closure portion of sterile connector end 37 is substantially a hollow rectangular shape with the longer pair of opposing walls arranged parallel with the channel walls 41*a* and 41*b* and the shorter pair of opposing walls arranged at its inner and outer surfaces. An actuating portion 38 is provided on the outer short wall and a compression portion 43 is provided on the inner shorter wall.

The closure portion of sterile connector end 37 is the located over a valve wall 39 fixed within the channel and spaced away from the channel walls 41*a* and 41*b*. The closure portion of sterile connector end 37 can thus be moved between two extreme positions—a closed position (FIG. 4A) and an open position (FIG. 4B)—by sliding past the valve wall 39 within the channel.

The flexible tubing 29 is arranged to extend through the valve means 27 such that a section of the flexible tubing 29 sits between the valve wall 39 and the compression portion 43. In the closed position, the closure portion of sterile connector end 37 is urged toward the outer perimeter of the base plate 15 by a spring 35. The spring 35 is positioned to act on the compression portion 43, urging it against the flexible tubing 29 and pinching it against the valve wall 39. Thus, in the closed position, the pinched section of tubing blocks the fluid communication conduit and prevents fluid flow.

To unblock the conduit, the closure portion of sterile connector end 37 is moved toward the open position by pressing the actuating portion 38, releasing the compression portion 43 from the valve wall 39 and allowing the pinched section of the flexible tubing to revert to its original shape and permitting fluid flow.

With the cell processing device installed in the cell processing unit, the valve means 27 is actuated by actuator 38 and opened while the auxiliary container 11 is compressed by plunger 103*a*. The actuator 38 may be configured so that the valve means 27 opens when the auxiliary container 11 is compressed. Alternatively, actuation may occur as a separate step, for example, when the auxiliary container 11 is received into the auxiliary container port 19. The actuation may occur automatically in conjunction with the compression of the auxiliary container 11, or may be controlled to happen independently.

In the example shown, the valve actuation is carried out by a linear actuator 38 located at the rear of the chamber 3 of the cell processing unit 1, which acts upon the closure portion of sterile connector end 37 to move it toward the open position. Thus, the valve means is normally closed and actuated to open only when fluid needs to be delivered to the primary container 13.

As shown in FIG. 3, each auxiliary container 11 is attached to a filling valve connector 26 in the form of a 4-way stopcock. The connector 26 comprises a Luer Lok™ port for filling via direct access to the auxiliary container 11. This port, which may be used for manually inserting fluids into the auxiliary container, does not have its own valve means 27 but is capped instead.

Two further capped Luer Lok™ ports are provided on base plate 15 for sampling/harvesting fluid, or gas exchange. A first port leads to the head space of the primary container, while a further port is connected to the base of the primary container 13.

Figure 5:
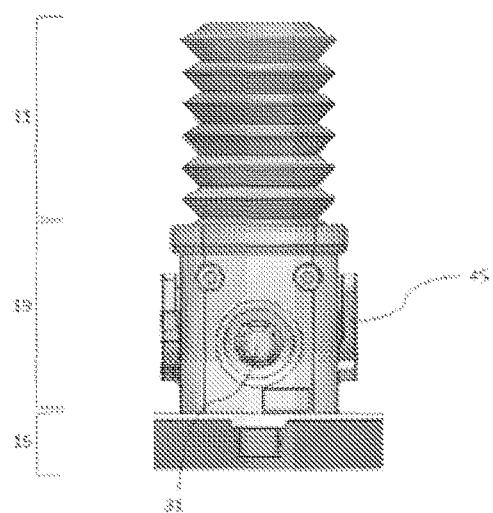
FIG. 5 illustrates an isolated side view of one auxiliary container port and auxiliary container of the cell processing device FIG. 2.

FIG. 5 depicts the filling port 31 and lever 45 mounted on the auxiliary container port 19. The lever 45 is provided in order to fill the auxiliary container 11 without allowing material to flow into the valve means 27 or primary container 13. The lever 45 is operatively connected to a 4-way stopcock, which forms the connector 26 in the example described above. At the fill position (lever pointing down), the filling port 31 is opened and flow of material through the port 31 is directed into the auxiliary container 11. Then, at the feed position (lever pointing up), the filling port 31 is closed and flow is directed from the auxiliary container 11 via the flexible tubing 29 and into the primary container 13.

Sterile Connectors

Figure 12:
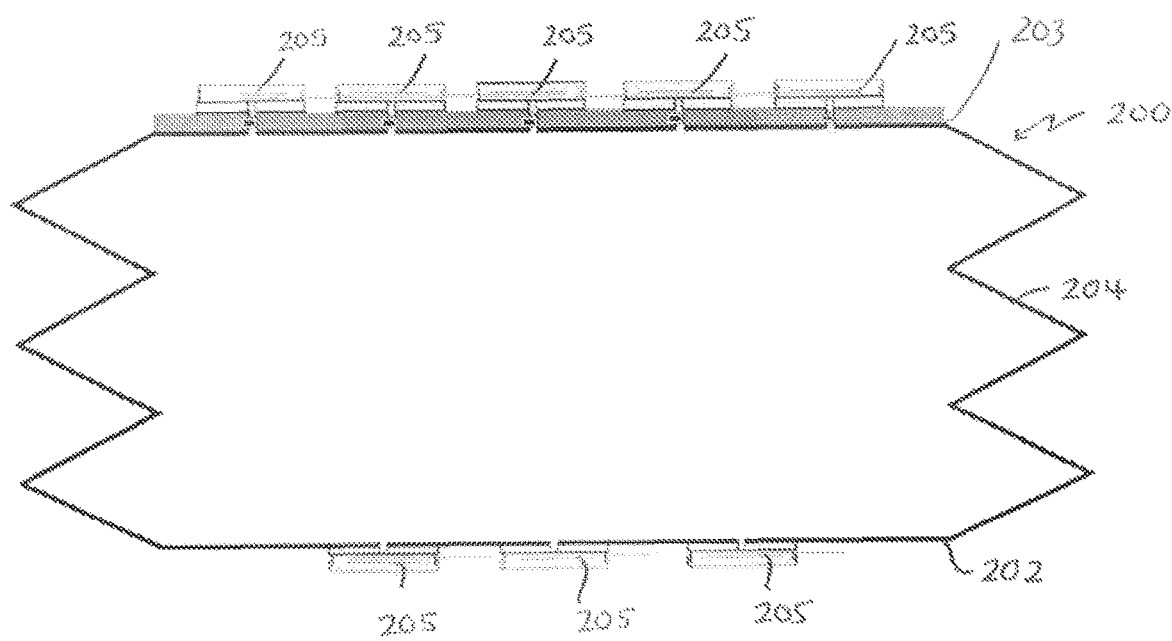
FIG. 12 shows a perspective view from the side of a representation of one embodiment of a cell processing container comprising a plurality of sterile connectors according to an embodiment of the disclosure.

FIG. 12 shows a cell processing container 200 according to an embodiment of the disclosure. Cell processing container 200 comprises a base section 202, a top section 203 and a wall element 204 arranged between the top section 203 and the housing 2. The wall element 204 is preferably composed of a flexible material. The wall element 204 is preferably compressible with respect to the top section 203 and the base section 202. The cell processing container 200 may thereby have a "concertina" or "bellows arrangement," e.g., it may have one or more z-folds in the wall element 204 arrangement.

The cell processing container 200 may comprise 1 sterile connector end and preferably comprises a plurality of connector ends 205. The connector ends 205 are preferably sterile. The sterile connector ends 205 are preferably located on the top section 203 and/or on the base section 202 of the cell processing container 200. The cell processing container 200 preferably comprises at least 1, at least 2, at least 3, at least 4, or at least 5 sterile connector ends 205. According to a preferred embodiment, the sterile connector ends 205 are embedded in the cell processing container 200. The sterile connector ends 205 enable an easy and sterile connection of auxiliary containers 11 to the cell processing container 200.

The cell processing container 200 may have any possible shape. In a preferred embodiment the cell processing container 200 has a circular, square, rectangular, elliptical, or triangular cross section.

In a preferred embodiment, when the cell processing container 200 has a circular shape, the sterile connector ends 205 are preferably connected to the top 203 and/or base 202 section in an essentially circular pattern. The cell processing container 200 also comprises a sterile connector end 205 in the center of the top 203 and the base 202. The sterile connector ends 205 are connected to the top 203 and/or base 202 section essentially symmetrically having essentially the same distance between the different connector ends 205. This enables an easier and possibly automated process of cell and/or gene therapy manufacturing. In an alternative embodiment, when the cell culture container 200 has a circular shape, a sterile connector end 205 are connected to the center of the top section 203 and base section 202.

Figure 13:
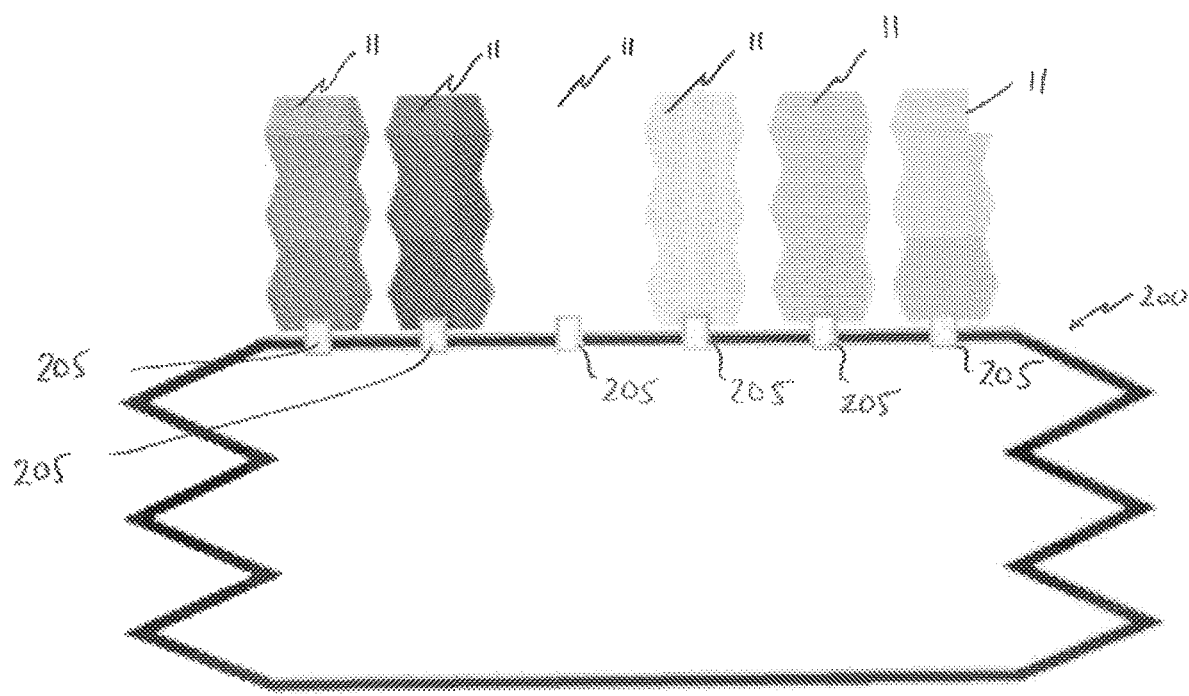
FIG. 13 shows a perspective view from the side of a representation of one embodiment of the cell processing system of the present disclosure.
Figure 14A:
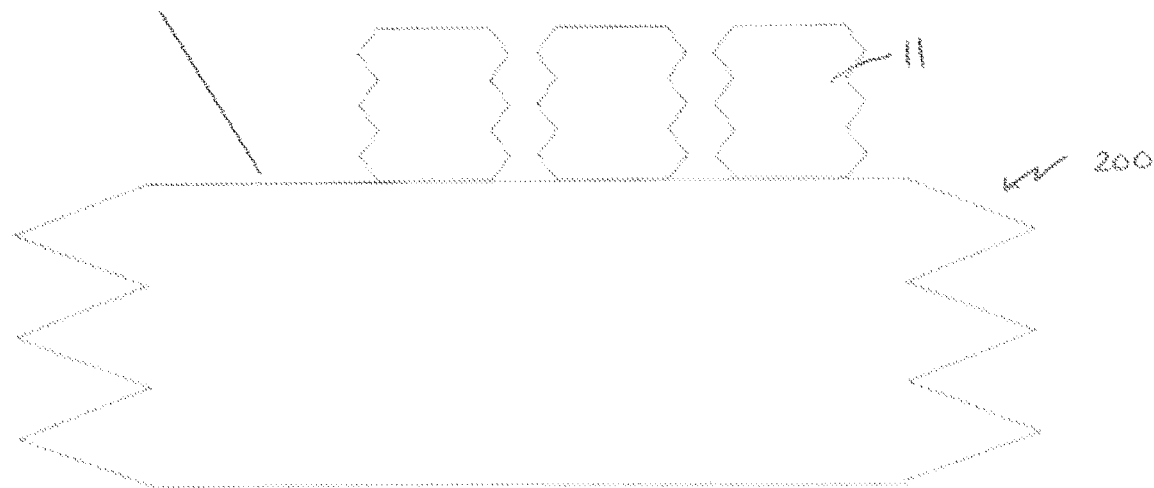
FIG. 14A shows a perspective view from the side of a representation of one embodiment of the cell processing system of the present disclosure, where auxiliary containers are connected to the cell processing container, leaving an empty auxiliary container port for a further auxiliary container to be connected.
Figure 14B:
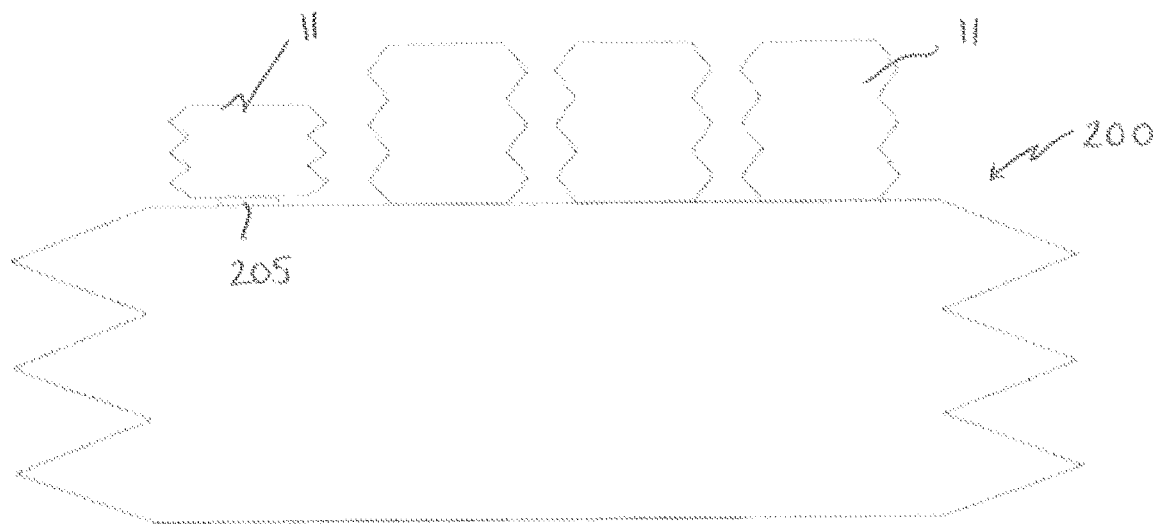
FIG. 14B shows a perspective view from the side of a representation of one embodiment of the cell processing system of the present disclosure, where an auxiliary container has been connected to the empty auxiliary container port of the cell processing container.

An embodiment of the present disclosure is shown in FIG. 13 and FIGS. 14A-14B, showing a cell processing system according to the present disclosure, comprising a cell processing container 200 as described above together with one or more auxiliary containers 11 attached to the cell processing container 200. The auxiliary containers 11 are preferably connected to the cell processing container 200 via sterile connector ends 205. The auxiliary containers 11 are preferably connected to the cell processing container 200 on the top section 203 and/or the base section 202. The auxiliary containers 11 may also be cell processing containers according to the disclosure comprising an embedded sterile connector end in a base portion of the auxiliary container 11.

In further embodiments such as the one shown in FIG. 2, the auxiliary containers 11 are fluidly coupled to the cell processing container 13 through a body portion 15. The body portion forms part of a cell processing platform 9. The auxiliary containers 11 each comprise a sterile connector end embedded in the base section of the auxiliary container 11. The embedded sterile connector end interconnects and sealingly engages with a corresponding sterile connector end in the body portion 15 of the cell processing platform 9. The cell processing container 13, being a primary container, is sealingly engaged with the bottom of the body portion 15 so as to form a fluid connection between the body portion 15 and the cell processing container 13.

The fluid conduit (not shown) between the sterile connector attaching the auxiliary container 11 to the body portion 15 and the fluid outlet (not shown) of the body portion 15 to which the cell processing container 13 is attached, comprises a pinch valve. The pinch valve is operable to open and close the fluid conduit in response to a valve actuator such that, as a compression force is applied to the respective auxiliary container 11, the contents of the auxiliary container can be transferred by the application of a compression force to the container. In alternative embodiments, the pinch valve may be replaced by a pressure-sensitive valve (e.g., a burst valve) such that the valve opens as a compression force is applied to the respective auxiliary container 11.

In the embodiment shown in FIGS. 14A and 14B, one or more of feed bellows of the auxiliary container 11 are pre-attached to the primary cell processing container 200 and prefilled with reagent (e.g., liquid) and stored in a refrigerator. The cell processing system shown in FIGS. 14A and 14B may be used for attaching heat labile components, such as viruses or cells, which need to be stored in at −80 degrees Celsius or in liquid nitrogen. Because, it is expensive to store the whole cell processing system at these temperatures, the embedded sterile connectors 205 in the feed bellows of auxiliary container 11 and in the top of the primary cell processing container 200 serve as a way to add the heat labile component(s) without use of an aseptic laminar flow hood or sterile tubing welders thus eliminating tube based connections and keeping the system compact.

Advanced blow molding techniques can be used to deposit a second (or even third), external, coating or layer of plastic impermeable to oxygen onto the wall, top and base of the auxiliary container. In this way, shelf life of the container in storage can be extended.

Figure 15A:
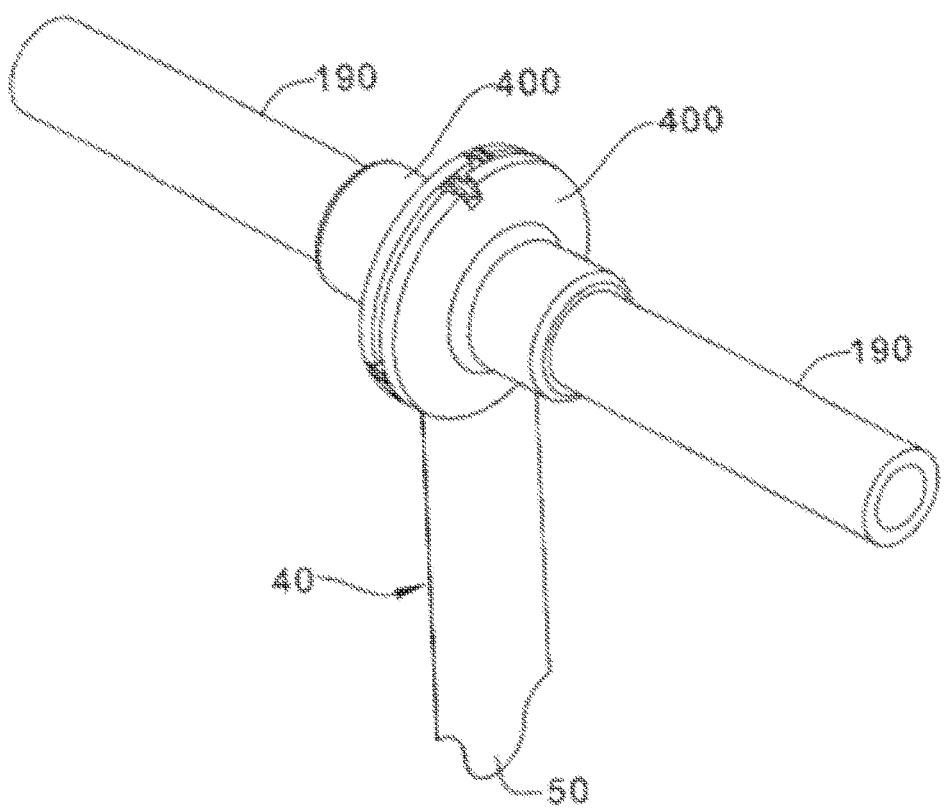
FIGS. 15A, 15B, 15C and 15D show a known sterile connector arrangement formed from two sterile connector ends.
Figure 15B:
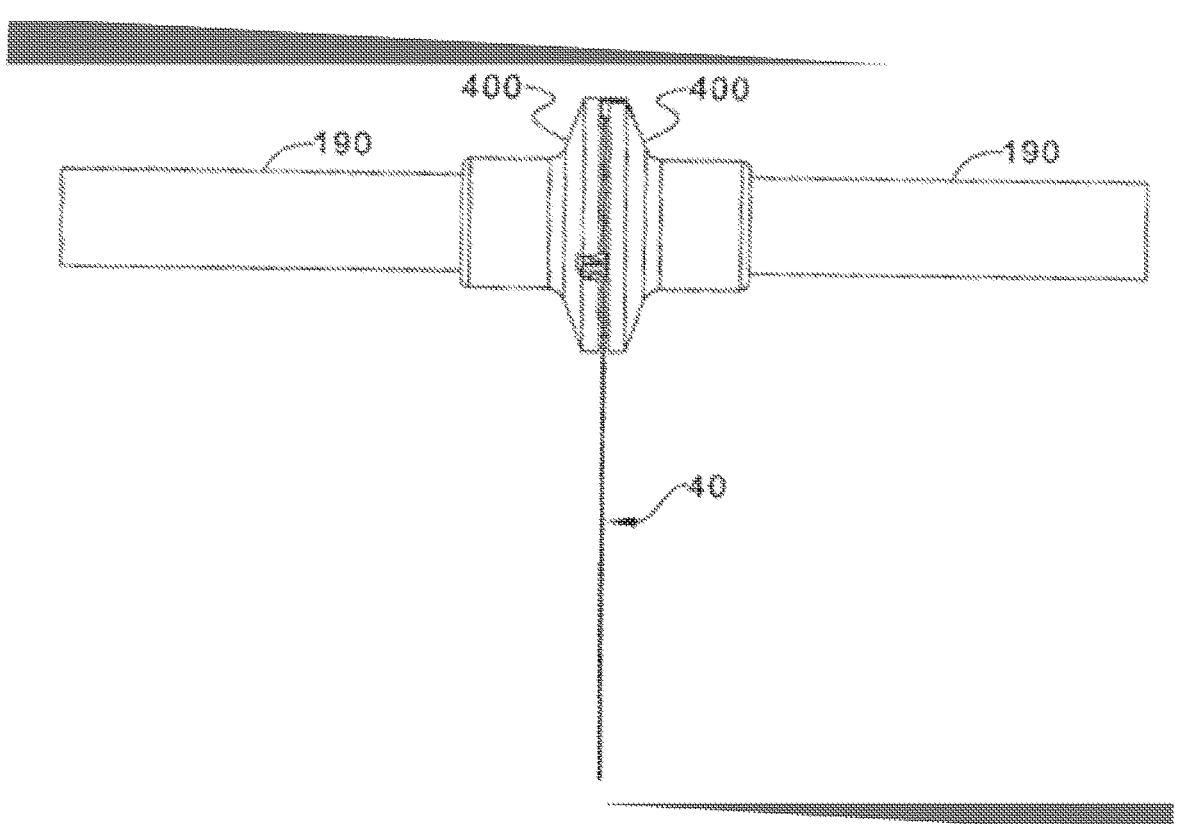
Figure 15C:
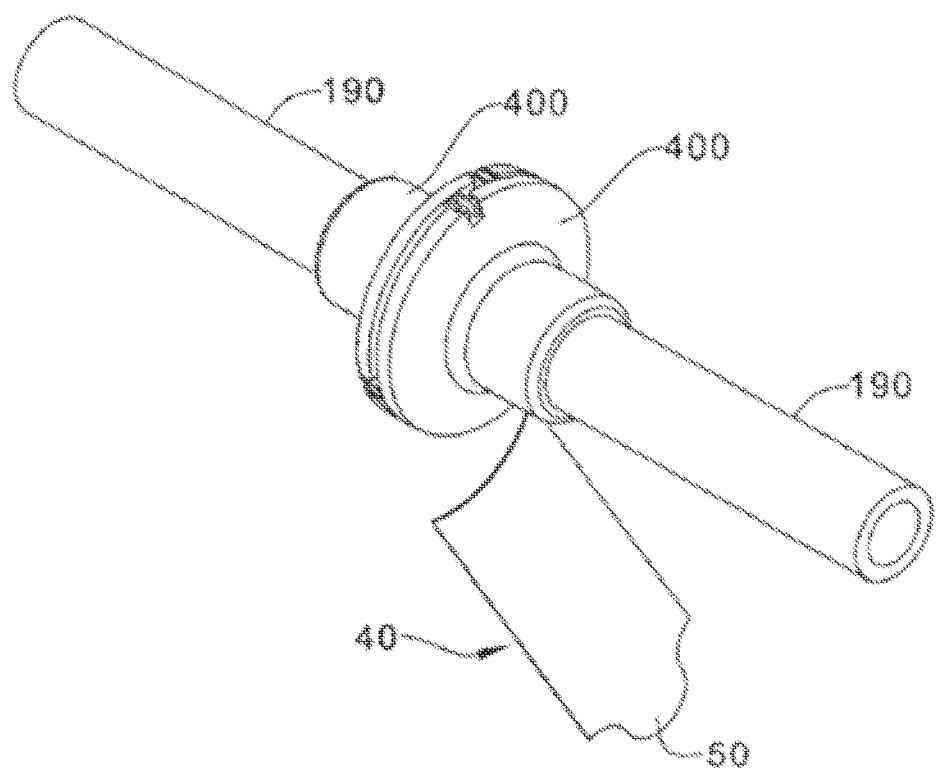
Figure 15D:
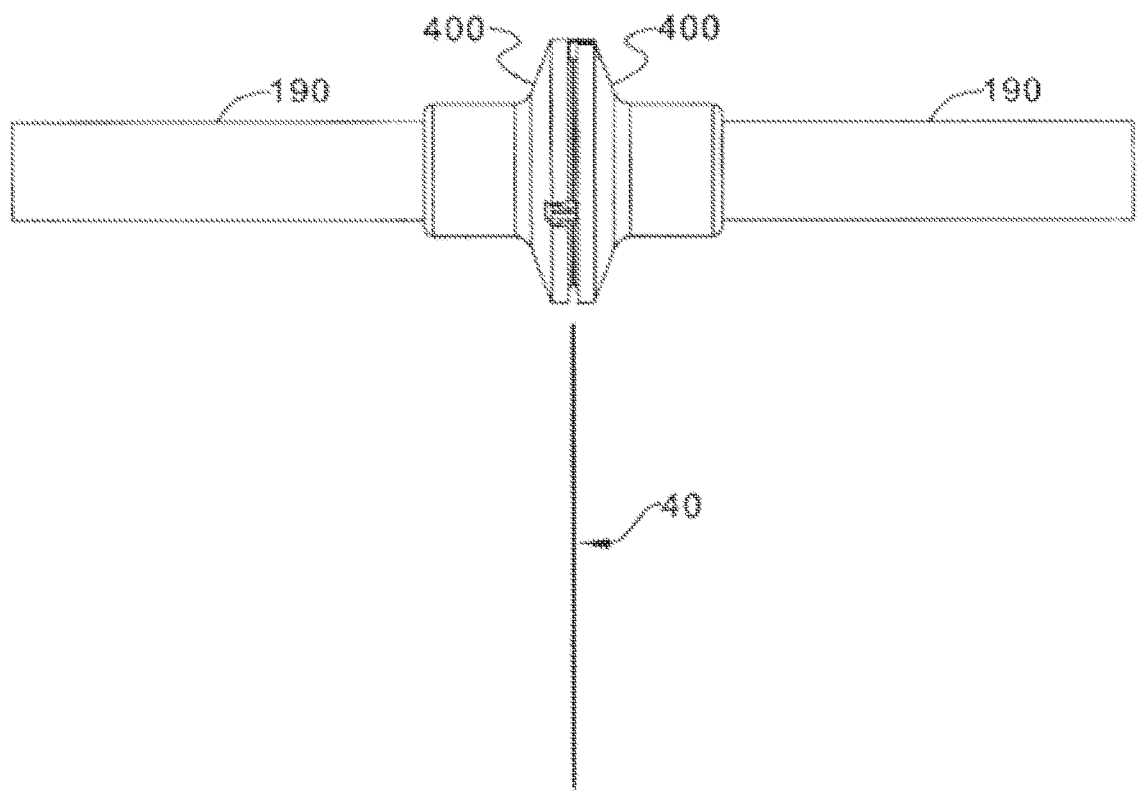

FIGS. 15A to 15D show an exemplary sterile connection between two sterile connector ends 400. The sterile connector ends 400 each have a mechanical connection (such as a screw thread) or latch (not shown) arranged in an internal circumferential manner on the sterile connector end 400. The internal circumferential latches provide the proper orientation of sterile connector end 400 relative to the other to ensure that the opposedly aligned adhesive members 40 attached to the sterile connector end 400 achieve a sterile fluid connection. In FIG. 15B, two adhesive members 40 are aligned so that the front second fold adhesive coating of each adhesive member 40 mirror each other. This alignment is important, as the rolled member 40 may be withdrawn in only one linear direction. Once the two front second fold adhesive coating surfaces are in contact, as shown in FIG. 15C, the member pull grip 50 is pulled away from the longitudinal axis of the sterile conduit 190 thereby exposing the conduit aperture (FIG. 15D). In FIGS. 15C and 15D, the rolled member 40 is completely withdrawn to an unfolded configuration and the conduit apertures are aligned to form a sterile corridor.

Figure 16A:
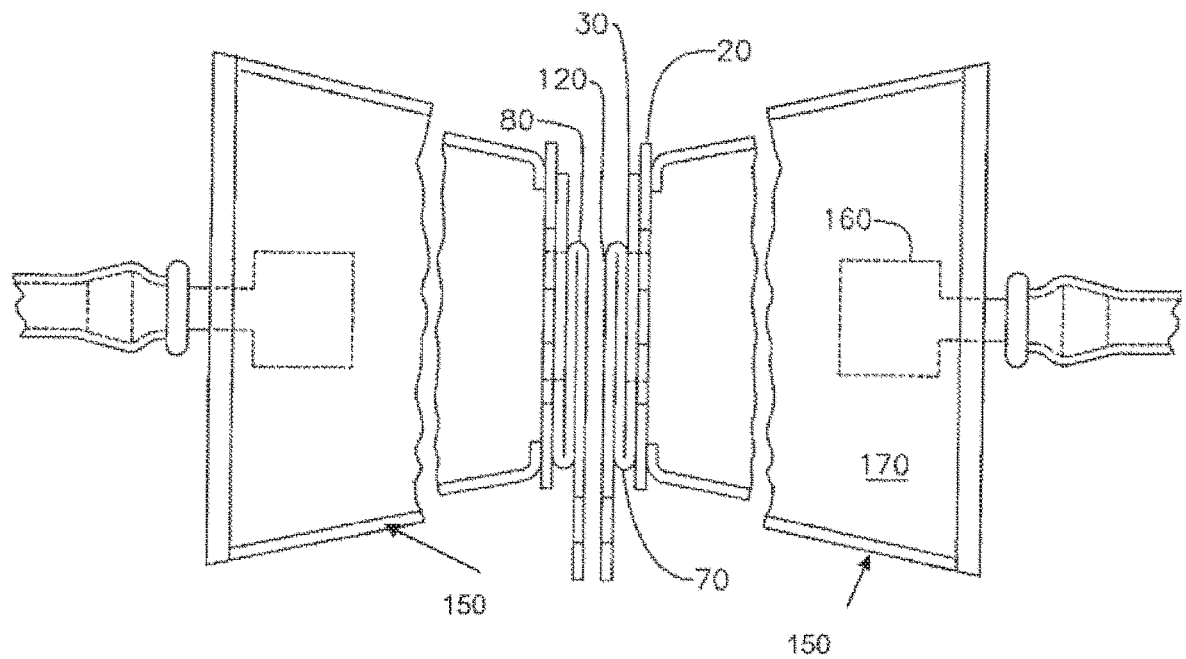
FIGS. 16A, 16B, 16C and 16D show the formation of a sterile connector from two known sterile connector ends.
Figure 16B:
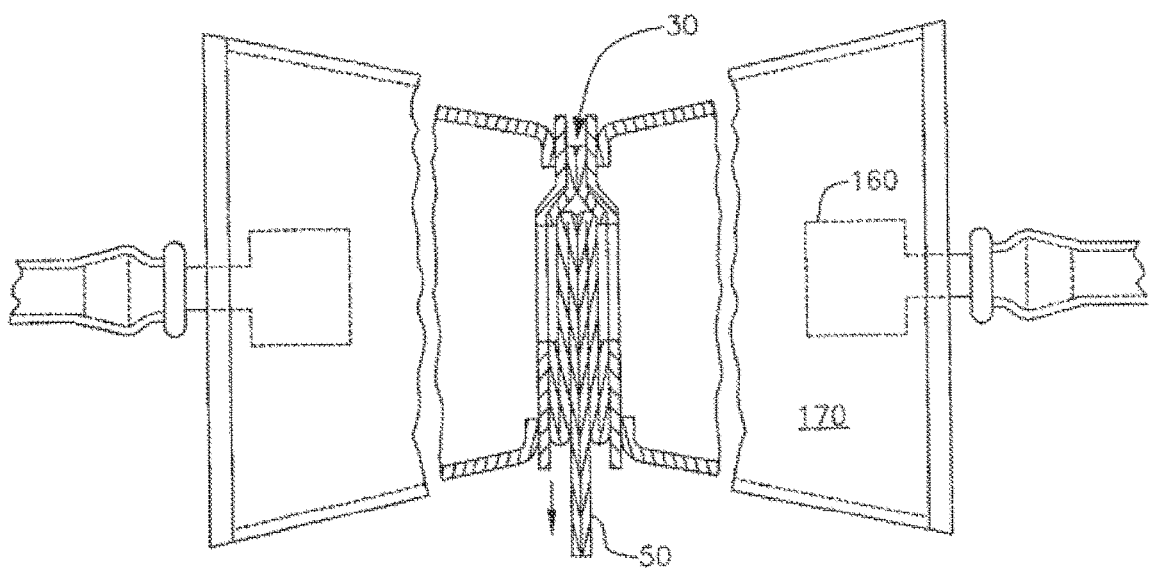
Figure 16C:
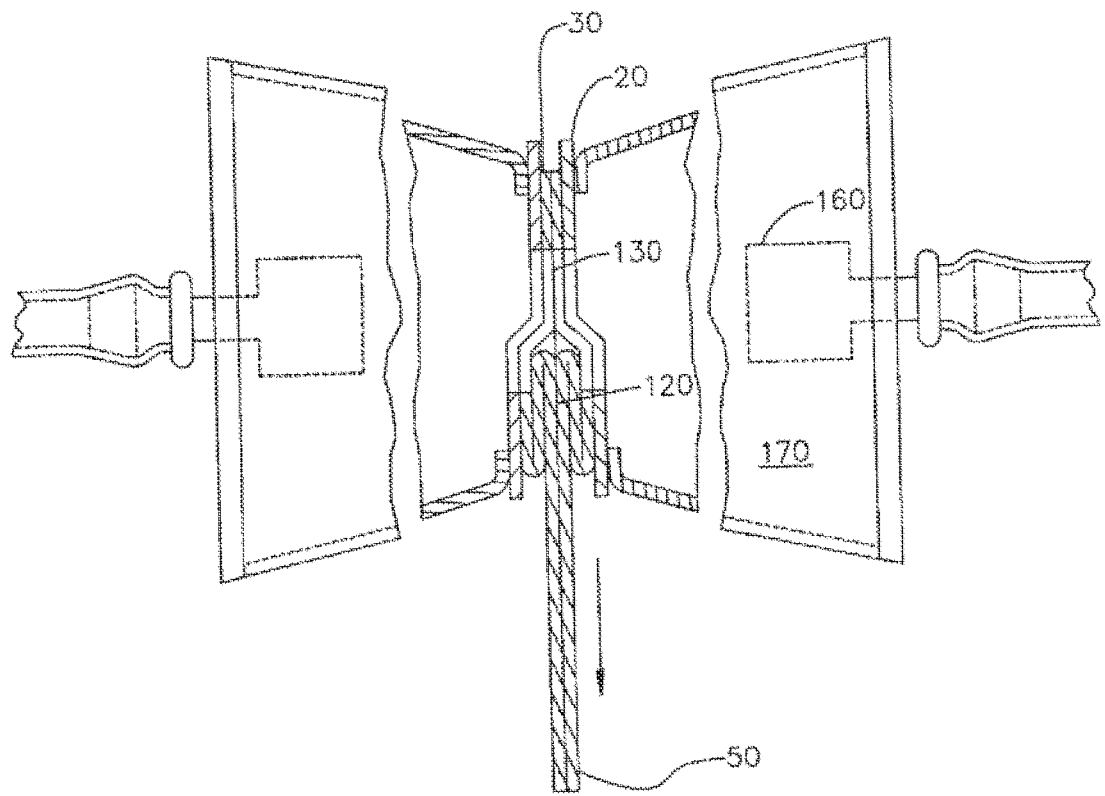
Figure 16D:
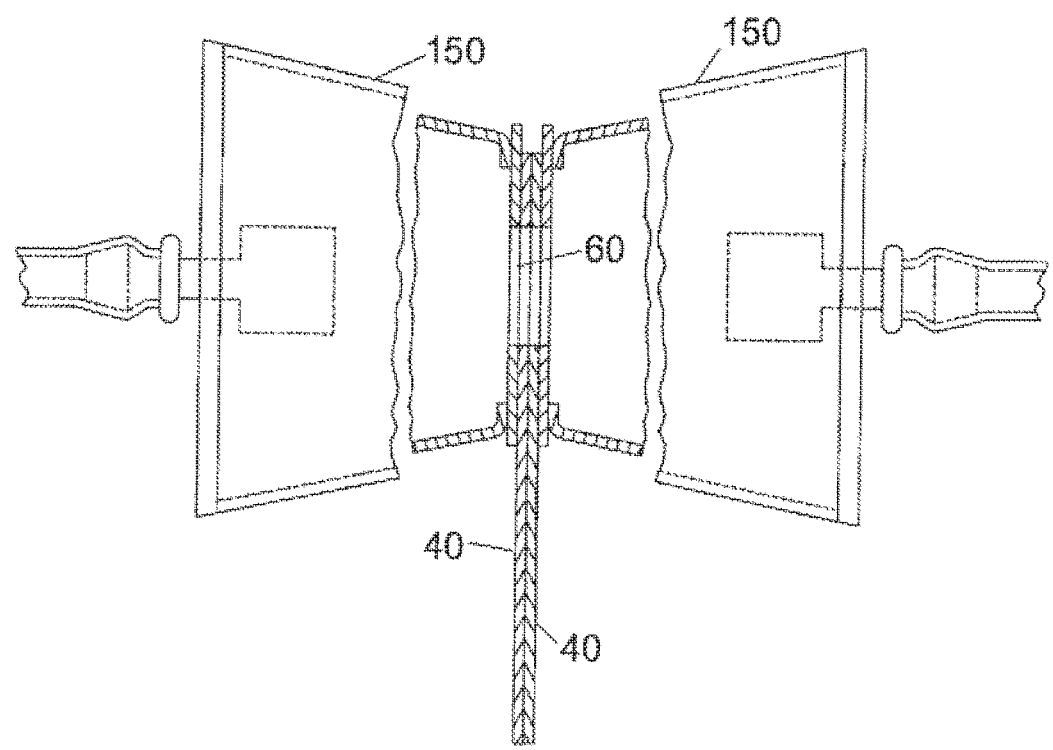

In FIG. 16A, two opposing sterile connector ends 150 are aligned so that the front second fold adhesive coating 80, 120 of each rolled membrane of the sterile connector ends 150 mirror each other. This alignment is important as the rolled membrane may be withdrawn in only one linear direction. Once the two front second fold adhesive coating 80, 120 surfaces are in contact, as shown in FIG. 16B, the entire adhesive surface areas come into contact thereby sealing each opposing sterile connector ends 150 together. In FIG. 16C, the membrane pull grip 50 is pulled away from the longitudinal axis of the sterile corridor thereby exposing the conduit aperture 60. In FIG. 16D, the rolled member 40 is completely withdrawn to an unfolded configuration and the conduit apertures 60 are aligned to form a sterile corridor between each sterile connector end 150.

Figure 17A:
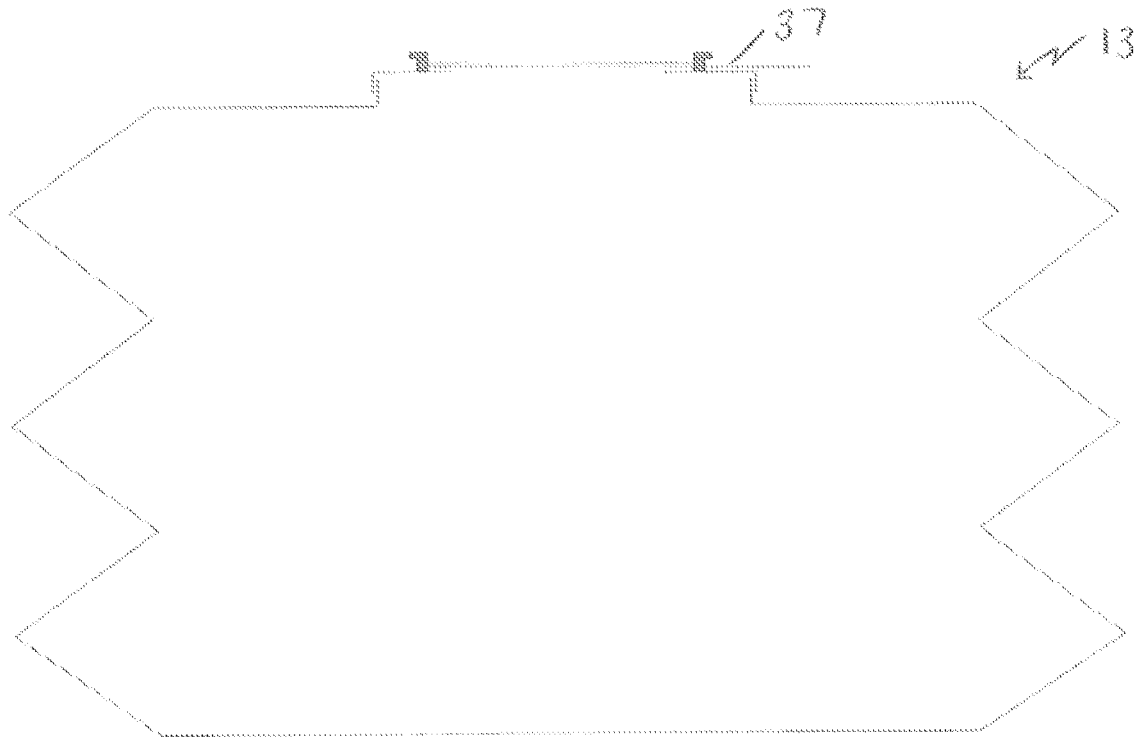
FIG. 17A shows a perspective view from the side of a representation of one embodiment of a cell processing container comprising a sterile connector end embedded therein.

FIG. 17A shows a cell processing container 13 having a sterile connector end 37 embedded in a top section of the container wall. The sterile connector end 37 forms one-half of a sterile connector when the cell processing container 13 is fluidly connected to the corresponding sterile connector end in an auxiliary container 11. In alternative embodiments, the cell processing container 13 is fluidly connected to the corresponding sterile connector end in a body portion 15 of a cell processing platform 9. The sterile connector end in a body portion 15 of a cell processing platform 9 being part of a primary container port of the platform.

Figure 17B:
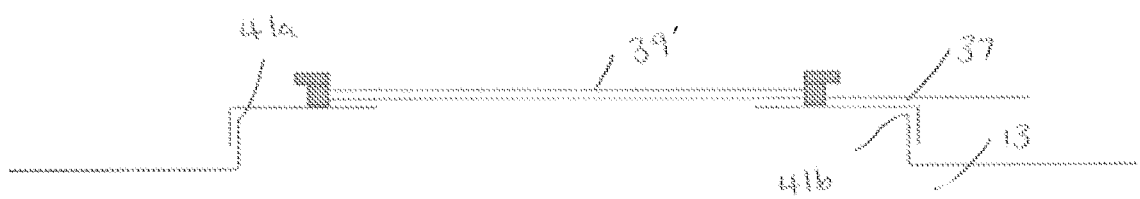
FIG. 17B shows a close view of the sterile connector end of the cell processing container of FIG. 15A.

FIG. 17B shows an exploded partial view of the sterile connector end 37 of FIG. 17A. FIG. 17B shows a male sterile connector end, being half of sterile connector, in a top wall of cell processing container 13. The sterile connector end 37 comprises a removable paper cap 39', which, when engaged with the removable paper cap of a further sterile connector end is removed, exposes the sterile surfaces enclosed by a screw cap engaged with screw threads of the sterile connector end 37 and creates a fluid connection through to the cell processing container lumen. Specifically, the removable paper cap is an anti-contamination pull tab, which is initially folded over the sterile connector end 37 and has an end protruding therefrom. The pull tab can then be pulled out to expose the sterile surfaces to each other.

Figure 17C:
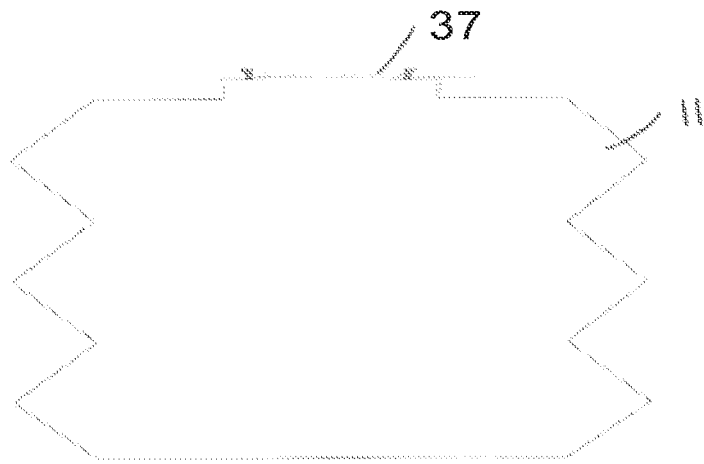
FIGS. 17C, 17d and 17E a perspective view from the side of a representation of an auxiliary container for a cell processing device and/or a cell processing system according to the disclosure comprising a sterile connector end and being prepared for filling with reagent.
Figure 17D:
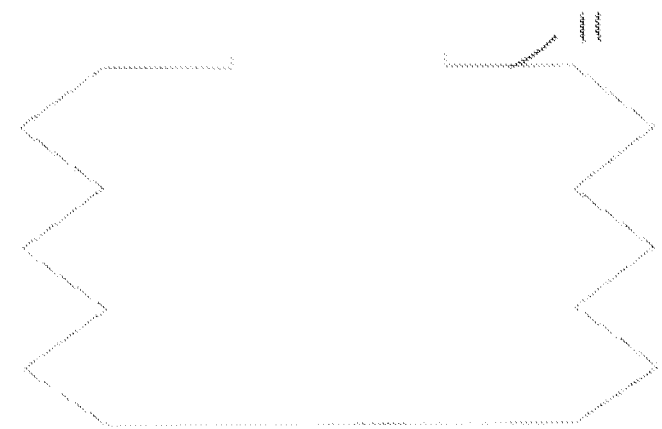
Figure 17E:
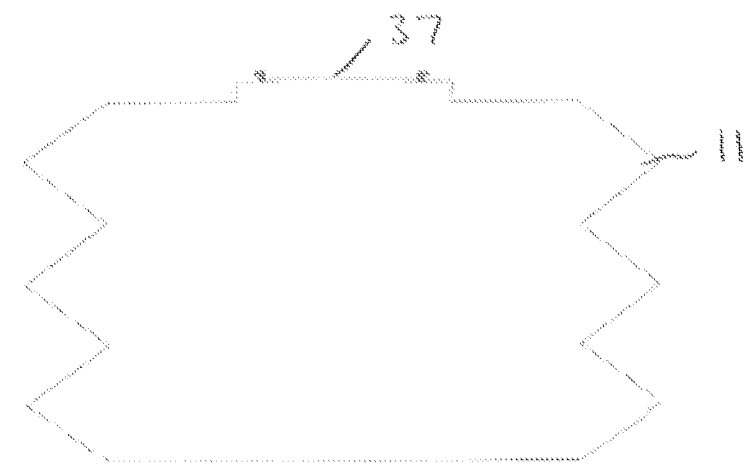

FIG. 17C to 17E depict an auxiliary container 11 being filled with media in a sterile process. The process can be manual or automated. In FIG. 17D the sterile connector end 37 is removed and media filled into the lumen of the auxiliary container 11. The filling of the auxiliary container 11 is performed under sterile conditions. In FIG. 17E, the sterile connector end 37 is replaced and the auxiliary container 11 stored at the appropriate temperature until it is needed for assembly of the cell processing system. Once filled and ready for use, the auxiliary container 11 is inverted and the sterile connector end 37 mated and connected with a corresponding sterile connector end on a primary container such as a cell processing container.

Figure 18A:
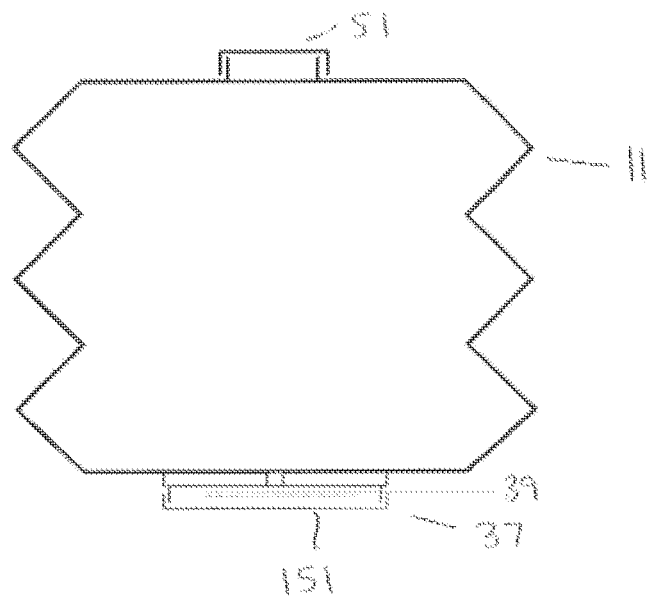
FIG. 18A shows a perspective view from the side of a representation of one embodiment of an auxiliary container comprising a sterile connector end embedded in a base section and a screw top cap in a top section.

In alternative embodiments such as the one depicted in FIG. 18A, the auxiliary container 11 has a screw cap 51 at one end and a sterile connector end 37 at the other. In this way, the integrity of the sterile connector end 37 can be maintained during storage of the auxiliary container 11 by inverting the auxiliary container 11 such that the media sits at the end of the auxiliary container 11 having the screw cap 51 and the sterile connector end 37 is free from any liquid contact.

The embedded sterile connector end 37 ensures that the auxiliary container 11 can be readily connected to an auxiliary container port of a cell processing platform 9 or directly to a cell processing container 13 in a cell processing system according to the disclosure.

FIG. 18A shows an auxiliary container 11 having a sterile connector end 37 protected by in an end cap 151 in the base section of the auxiliary container 11. The auxiliary container 11 also has a screw cap 51 in the top section of the container to allow for filling of the lumen of the container with media or the like. The screw cap 51 is compatible with automated media filling techniques and apparatus.

The sterile connector end 37 facilitates fluid connection between the lumen of the auxiliary container and the contents in it, with a cell processing container 13 having a corresponding sterile connector end in a top section of the cell processing container 13. In order to access the sterile connector end 37 in the base section of the auxiliary container 11, the cap 151 is removed, the sterile connector end 37 can then be mated into sealing engagement with a corresponding sterile connector end on the cell processing container 13. In alternative embodiments, the sterile connector end 37 can be mated into sealing engagement with a corresponding sterile connector end on a cell processing platform. More specifically, the sterile connector end 37 can be mated into sealing engagement with a corresponding sterile connector end in the auxiliary container port 19 on a cell processing platform 9.

Advanced blow molding techniques can be used to deposit a second (or even third), external, coating or layer of plastic impermeable to oxygen onto the wall, top and base of the auxiliary container. In this way, shelf life of the container in storage can be extended.

Figure 18B:
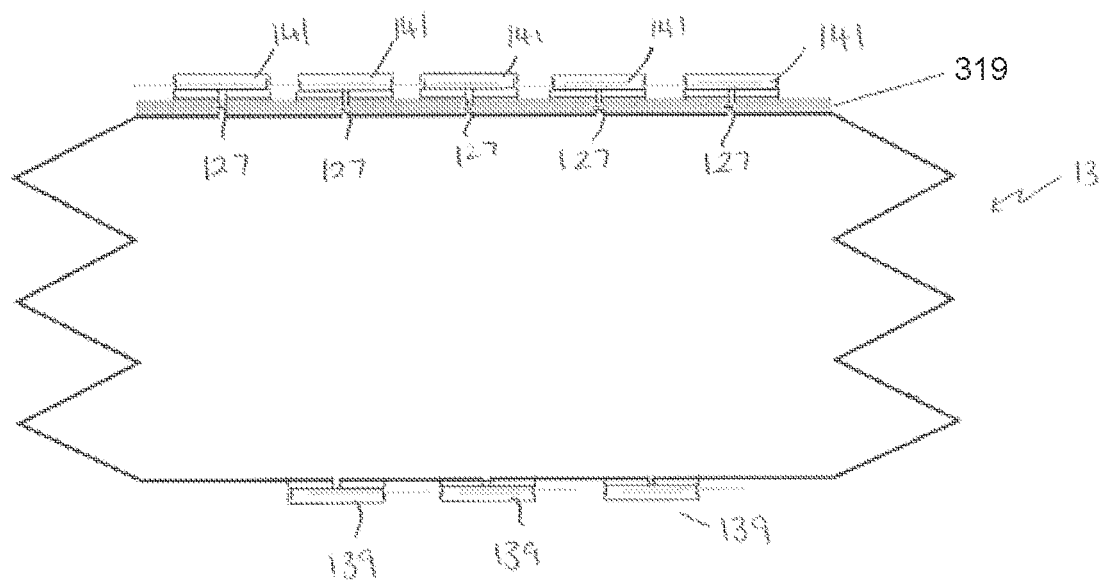
FIG. 18B shows a perspective view from the side of a representation of one embodiment of a cell processing container comprising a plurality of sterile connector ends embedded in a top and a bottom section.

FIG. 18B shows a cell processing container (reactor bellows) 13 comprising a plurality of bottom sterile connectors, being embedded sterile connector ends 139, in the base section of the cell processing container 13. In the depicted embodiments, the cell processing container 13 (e.g., reactor bellows) is fitted with a plurality of sterile connector ends 141 in a top section of the cell processing container 13 for connection of a plurality of auxiliary containers 11. The auxiliary containers 11 may contain media and/or cell nutrients required for cell culture. Alternatively, the auxiliary containers may be for sampling or waste removal from cell processing container 13. In a sampling arrangement, the cell processing container (e.g., reactor bellows) 13 may be fluidly connected via a pinch valve to a removable auxiliary container 11. The pinch valve is opened and then the auxiliary container 11 is expanded to take the sample from the cell processing container 13. The pinch valve is then closed before detaching the sample auxiliary container 11. The connection could be via Luer Lok or similar, which maintains a sterile barrier once the pinch valve is closed. Thus, samples may be removed from the cell processing container 13. The cell processing container 13 (e.g., reactor bellows) is fitted with a plurality of sterile connector ends 139 in a base section of the cell processing container 13 for connection to a plurality subsequent collection/processing bellows (not shown). Pinch valves 127 are housed between the sterile connector ends 141 and the cell processing container 13, which pinch valves 127 can be used to switch on/off the flow of feeds from the auxiliary containers 11. Such valve activation is useful/necessary, for example, if only partial volumes are needed or feed needs to be added from a single auxiliary container at two or more time points.

In alternative embodiments, pinch valves can be embedded in the outlet tubing from each auxiliary container 11.

In yet further alternative embodiments, the pinch valves can be pressure actuated to open when compression force is applied to the respective auxiliary container 11.

Figure 18C:
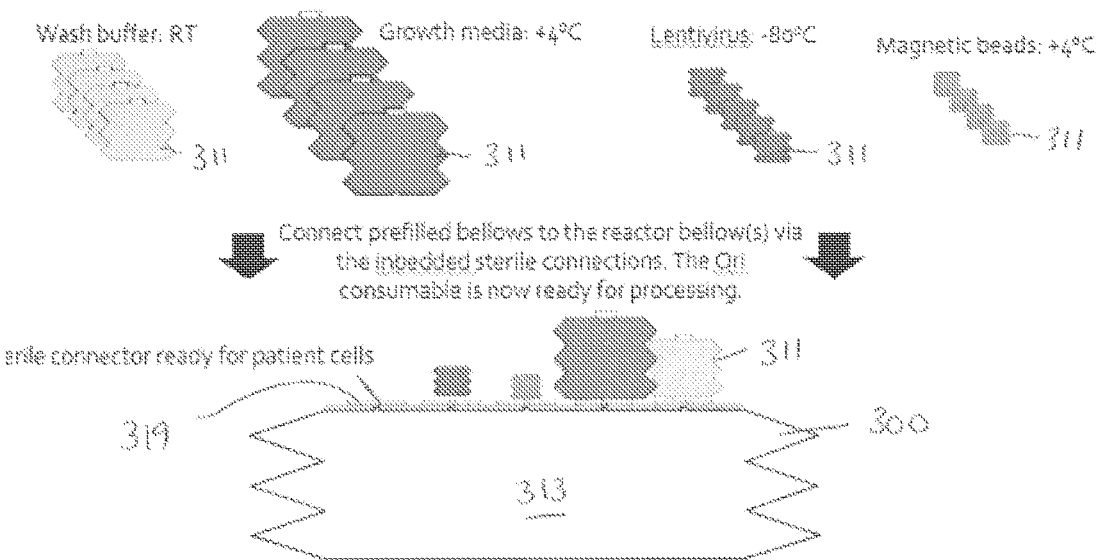
FIG. 18C shows a schematic representation of a number of prefilled auxiliary containers being connected to a cell processing container to create a cell processing system according to the disclosure having a sterile connector end in an auxiliary container port for receiving a further auxiliary container containing patient cells.

FIG. 18C shows the use of prefilled auxiliary containers 311 in a cell processing system 300 according to the disclosure. Four auxiliary containers 311 are prefilled with wash buffer and are stored at room temperature. Four further auxiliary containers 311 are prefilled with growth media and are stored at 4 degrees Celsius. Five auxiliary containers 311 are prefilled with Lentivirus are stored at −80 degrees Celsius. Four further auxiliary containers 311 are prefilled with media incorporating magnetic beads and stored at 4 degrees Celsius. One each of the prefilled auxiliary containers 311 are connected to the cell processing container 313 via sterile connector ends embedded in the base portion of each auxiliary container 311 and in the top of the cell culture container 311. An auxiliary container port 319 remains empty and ready for receiving a container including patient cells. It should be appreciated that in alternative embodiments, the cell processing system 300 comprises a different number of prefilled auxiliary containers 311 according to the present disclosure. For example, each set of prefilled auxiliary containers 311 may comprise 10s or even 100s of auxiliary containers 311.

The cell processing system including the auxiliary containers 311 and the cell processing container 313 is now ready for processing in a cell processing unit according to the disclosure.

Figure 18D:
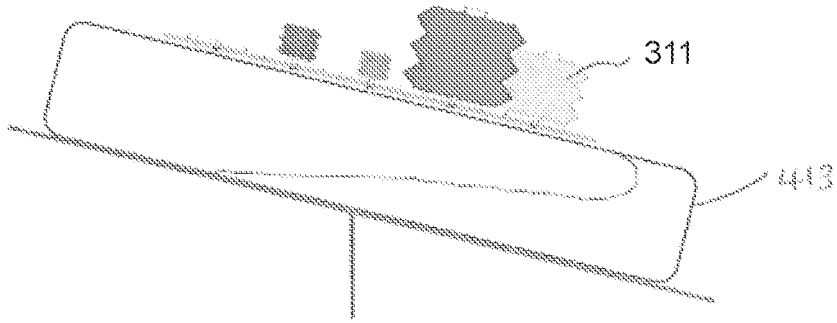
FIG. 18D shows a schematic representation of a number of prefilled auxiliary containers being connected to a single use wave container to create a cell processing system according to the disclosure having a sterile connector end in an auxiliary container port for receiving a further auxiliary container containing patient cells.
Figure 18E:
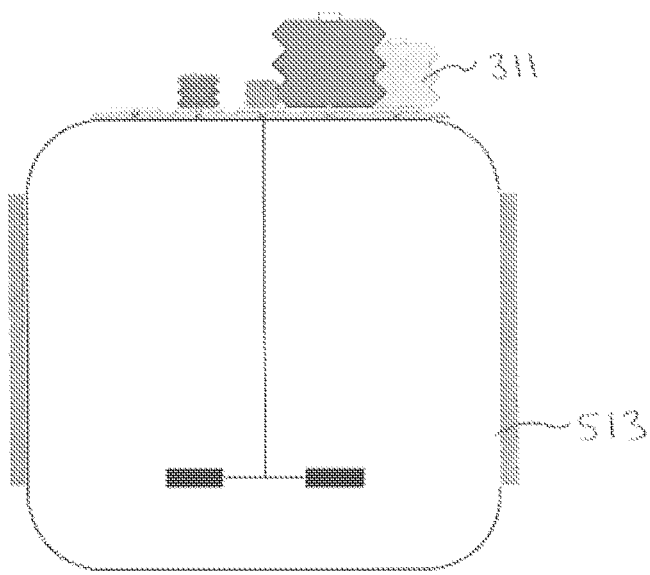
FIG. 18E shows a schematic representation of a number of prefilled auxiliary containers being connected to a CSTR bioreactor to create a cell processing system according to the disclosure having a sterile connector end in an auxiliary container port for receiving a further auxiliary container containing patient cells.

FIGS. 18D and 18E shows the prefilled auxiliary containers 311 housed on a conventional single use wave bioreactor 413 and CSTR bioreactor 513.

The cell processing unit, cell processing platform, cell processing device and cell processing container according to the disclosure may be used in any chemical, biological or separation process. Unit processes (e.g., steps) of such processes may be undertaken. The cell processing device, in conjunction with the cell processing unit and, optionally, at least one cell processing container of the disclosure may be used in cell culture processes (e.g., culturing, manipulating, expanding or storing cells) or in gene modification processes (e.g., steps including purifying, genetically modifying, recovery and wash processes). Other suitable unit processes that can be performed in the cell processing unit, platform, device and container of the disclosure include but are not limited to purification (e.g., affinity, size), washing, settling, centrifugation, filtration, chromatography, magnetic bead processes, transduction, electroporation, novel hydrogels, shipping and thawing, expansion of cells in culture, genetic modification and cryopreservation.

A cell processing device and a cell processing container of the disclosure are each suitable for cell culture and processing of cells, including the use of the container in cell therapy, gene therapy vector production and/or exosome production. A container or device of the disclosure may be suitably sterilized prior to use (e.g., by gamma irradiation or other means). Optionally the internal surface of the container may be coated with or comprise biologically active agents, which can act on the cells in culture and/or induce differentiation.

The cell processing equipment described herein may be used in cell manufacturing and/or gene therapy manufacturing processes involving any suitable cell or gene type. For example, the device of the disclosure may be used to culture any prokaryotic or eukaryotic cell, suitably an animal cell, e.g., a mammalian, cell. The cells may be human or non-human. Examples of sources of suitable non-human cells include, rodents such as mice, rats, and guinea-pigs, as well as ungulate animals selected from ovine, caprine, porcine, bovine and/or equine species, or non-human primate species. However, the cells may be bacteria, yeast, fungi or plant cell in origin also.

The cells may be of any type including somatic cells and non-somatic cells. The cells may be stem cells derived from any stage of development of the embryo, fetus or adult animal. The cells may be genetically modified cells, such as chimeric antigen receptor T-cells (CARTs). The cells may be from a deposited cell line, such as genetically-modified Chinese Hamster Ovary (CHO) cells to produce recombinant proteins.

For example, embryonic stem (ES) cells, including cells of non-human origin. The cells may be derived from a deposited cell line, such as an ES cell line. The ES cells may be derived from means that do not necessitate the destruction of a human embryo such as parthenogenetic activation, as described in WO 2003/046141. The cells may be cells of a cancer or a hybridoma, which can be caused to proliferate in culture and/or produce monoclonal antibodies. The cells may also be derived from the result of somatic cell nuclear transfer (SCNT) in which the nucleus of a somatic cell is placed into an enucleated oocyte.

The cells may be pluripotent stem cells, for example, primate pluripotent stem (pPS) cells, for example, human embryonic stem (hES) cells. Where the cells are stem cells, the source may be from any tissue of the body, including mesenchymal stem cells (including umbilical cord derived stem cells), neural stem cells or hematopoietic stem cells. Also included are induced pluripotent stem (iPS) cells.

The present disclosure therefore provides for the processing of cells within a single device with multiple unit processes taking place as desired within the cell processing device via delivery/extraction of desired reagents, waste, cells, or product into or from one or more auxiliary containers in fluid communication with the primary container, thereby avoiding the risk of contamination. The system is simpler to use and further avoids the complexity of existing approaches. The disclosure provides for the safer processing of cells with improved reproducibility and ease of use.

The disclosure also provides for the extraction of cells from a patient (biopsy, such as blood or bone marrow), separation of cells, processing of cells (including cytokine stimulation and/or genetic modifications), solid-liquid separations and loading into a delivery device where the cells can be cultured in the same device throughout the entire process.

In embodiments of the disclosure, cell processing containers for performing unit operations in cell and/or gene therapy manufacturing can be assembled in any configuration. In this way, a cell processing system may be provided within which a wide variety of processes (both biological, chemical and separations) can be undertaken. Similarly, the cell processing system may comprise a cell processing platform of the disclosure in conjunction with one or more cell processing containers. In this way it is possible to provide a multistage bioreactor operable to perform one or more unit operations in cell and/or gene therapy manufacturing. Because each cell processing container is based on a concertina arrangement (which can act as a pump) there is no need for pumps and complex sets of tubing/pipes. The system therefore shrinks the space needed for any given manufacturing process. A cell processing system according to the disclosure is particularly well suited for autologous (patient specific) cell and gene therapy where one needs to run a whole manufacturing run for each patient. Using traditional manufacturing approaches is not feasible when scaling up to over 5000 patients/year given the amount of space needed to run so many parallel manufacturing runs.

While various inventive embodiments have been described and illustrated herein, those having ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all structure, parameters, dimensions, materials, functionality, and configurations described herein are meant to be an example and that the actual structure, parameters, dimensions, materials, functionality, and configurations will depend upon the specific application or applications for which the inventive teachings is/are used.

Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, and method described herein. In addition, any combination of two or more such features, systems, articles, structure, materials, kits, functionalities, steps, and methods, if such are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, as noted, various inventive concepts are embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terminology used herein was chosen to best explain the principles of the one or more embodiments, practical applications, or technical improvements over current technologies, or to enable understanding of the embodiments disclosed herein. As described, details of well-known features and techniques may be omitted to avoid unnecessarily obscuring the embodiments of the present disclosure.

References in the specification to "one embodiment," "an embodiment," "an example embodiment," or the like, indicate that the embodiment described may include one or more particular features, structures, or characteristics, but it shall be understood that such particular features, structures, or characteristics may or may not be common to each and every disclosed embodiment of the present disclosure herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

What is currently claimed:

1. A cell processing method configured for at least one of cell and gene therapy manufacture, the method comprising:
    introducing a cell population of interest into a primary container located on and fluidly connected with a bottom of a body portion of a cell processing platform, wherein the cell processing platform is mounted within a housing of a cell processing unit, and wherein the primary container is compressible and comprises a first end, a second end arranged substantially parallel with the first end, and a wall element arranged between the first end and the second end, the wall element of the primary container being composed of a flexible material;
    sequentially adding one or more reagents from one or more auxiliary containers, located on and fluidly connected with a top of the body portion with the primary container fluidly connected to the one or more auxiliary containers via the body portion and wherein the one or more auxiliary containers are compressible, to the primary container, by exerting a compression force on the one or more auxiliary containers via a first actuator within the housing of the cell processing unit, in order to effect one or more desired unit operations in cell and gene therapy manufacture;
    culturing the cell population of interest in the primary container; and
    exerting a force on the primary container, wherein the force comprises compression or expansion of the primary container, and wherein the force is applied via a second actuator within the housing of the cell processing unit.

2. The method of claim 1, further comprising:
    detecting at least one of a position and location of the cell processing platform.

3. The method of claim 1, further comprising driving the cell processing platform.

4. The method of claim 3, wherein driving comprises rotating the cell processing platform.

5. The method of claim 4, wherein rotation is imparted on a surface of the body portion via a drive-wheel.

6. The method of claim 1, further comprising connecting the cell processing platform with at least one other additional cell processing platform or an additional component via a sterile connector.

7. The method of claim 6, wherein the sterile connector fluidly connects the cell processing platform with the at least one other additional cell processing platform or the additional component.

8. The method of claim 6, wherein the sterile connector is configured to connect to a further sterile connector end.

9. The method of claim 6, wherein the sterile connector is configured to connect to the primary container of the cell processing platform.

10. The method of claim 6, wherein the sterile connector is a genderless sterile connector.

11. The method of claim 1, further comprising sampling the contents of the primary container.

12. The method of claim 1, further comprising transferring at least one gas into or out of the primary container.

13. The method of claim 1, further comprising sealingly engaging the primary container with a second primary container.

14. The method of claim 1, wherein the method comprises tracking at least one of a position and location of the cell processing platform.

15. The method of claim 1, wherein the first actuator comprises a feed bellows plunger and the second actuator comprises a reactor plunger.

* * * * *